(12) United States Patent
Zhou et al.

(10) Patent No.: US 8,500,849 B2
(45) Date of Patent: *Aug. 6, 2013

(54) REACTIVE GAS DETECTION IN COMPLEX BACKGROUNDS

(75) Inventors: Xin Zhou, Rancho Cucamonga, CA (US); Xiang Liu, Phoenix, AZ (US); Alfred Feitisch, Los Gatos, CA (US); Gregory M. Sanger, Chico, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/428,626

(22) Filed: Mar. 23, 2012

(65) Prior Publication Data

US 2012/0185179 A1    Jul. 19, 2012

Related U.S. Application Data

(63) Continuation of application No. 12/911,666, filed on Oct. 25, 2010, now Pat. No. 8,152,900, which is a continuation-in-part of application No. 12/763,124, filed on Apr. 19, 2010, now Pat. No. 7,819,946, which is a continuation of application No. 12/101,890, filed on Apr. 11, 2008, now Pat. No. 7,704,301.

(60) Provisional application No. 60/923,005, filed on Apr. 11, 2007, provisional application No. 61/405,589, filed on Oct. 21, 2010.

(51) Int. Cl.
*B01D 59/26* (2006.01)

(52) U.S. Cl.
USPC ...... 95/90; 95/136; 95/235; 96/413; 423/210; 73/23.2; 73/23.21; 73/23.23; 73/863; 702/24

(58) Field of Classification Search
USPC .. 95/90, 136, 235; 96/413; 426/210; 73/23.2, 73/23.21, 23.23, 863; 702/24
See application file for complete search history.

(56) References Cited

U.S. PATENT DOCUMENTS

| | | | | |
|---|---|---|---|---|
| 7,704,301 B2 * | 4/2010 | Zhou et al. | | 95/90 |
| 7,819,946 B2 * | 10/2010 | Zhou et al. | | 95/90 |
| 8,152,900 B2 * | 4/2012 | Zhou et al. | | 95/90 |
| 2004/0034480 A1 | 2/2004 | Binder | | |
| 2006/0011844 A1 | 1/2006 | Oka et al. | | |

FOREIGN PATENT DOCUMENTS

DE    3619301 A1    12/1987

OTHER PUBLICATIONS

Translation of DE 3619301 Kaesler, Dec. 10, 1987.*
Weldon, et al., "H2S and C02 gas sensing using DFB laser diodes emitting at 1.57 mum", Sensors and Actuators B, vol. 29, pp. 101-107 (1995).

* cited by examiner

*Primary Examiner* — Christopher P Jones
(74) *Attorney, Agent, or Firm* — Mintz Levin Cohn Ferris Glovsky and Popeo, P.C.

(57) ABSTRACT

A differential absorption spectrum for a reactive gas in a gas mixture can be generated for sample absorption data by subtracting background absorption data set from the sample absorption data. The background absorption data can be characteristic of absorption characteristics of the background composition in a laser light scan range that includes a target wavelength. The differential absorption spectrum can be converted to a measured concentration of the reactive gas using calibration data. A determination can be made whether the background composition has substantially changed relative to the background absorption data, and new background absorption data can be used if the background composition has substantially changed. Related systems, apparatus, methods, and/or articles are also described.

18 Claims, 12 Drawing Sheets

REACTIVE GAS DETECTION IN COMPLEX BACKGROUNDS

CROSS-REFERENCE TO RELATED APPLICATIONS

This application is a continuation of U.S. patent application Ser. No. 12/911,666 filed on Oct. 25, 2010 and issued on Apr. 10, 2012 as U.S. Pat. No. 8,152,900, which claims the benefit under 35 U.S.C. §119(e) of U.S. Provisional patent application Ser. No. 61/405,589 filed on Oct. 21, 2010 and entitled "Dynamic Reconstruction of a Calibration State of An Absorption Spectrometer", and which is also a continuation-in-part of U.S. patent application Ser. No. 12/763,124 filed on Apr. 19, 2010 and issued on Oct. 26, 2010 as U.S. Pat. No. 7,819,946, which is a continuation of U.S. patent application Ser. No. 12/101,890 filed on Apr. 11, 2008 and issued on Apr. 27, 2010 as U.S. Pat. No. 7,704,301 which claims the benefit under 35 U.S.C. §119(e) of U.S. provisional patent application Ser. No. 60/923,005 filed on Apr. 11, 2007 and entitled "Detection of Hydrogen Sulfide in Hydrocarbon Backgrounds. The disclosures of all documents listed in this paragraph are incorporated by reference herein in their entireties.

FIELD

The subject matter described herein relates to detection of reactive gases, such as for example acidic or caustic gas-phase compounds, in gas mixtures containing a complex mixture of background gases.

BACKGROUND

Measurement of caustic and acidic reactive gases, such as for example hydrogen sulfide ($H_2S$), hydrogen chloride (HCl), hydrogen fluoride (HF), hydrogen cyanide (HCN), hydrogen bromide (HBr), arsine ($AsH_3$), phosphine ($PH_3$), and ammonia ($NH_3$), in gas streams containing a complex mixture of potentially interfering analytes presents a number of difficulties. Accurate characterization of such analytes can be quite important in a wide range of applications, including but not limited to petroleum product processing, extraction, transportation, and combustion, and numerous industrial processes.

The reactive gases discussed herein, as well as other gases with similar properties, can present significant environmental and human safety hazards. Hydrogen sulfide, for example, is a gas with a characteristic "rotten egg" odor that is highly flammable in air (in a concentration range of approximately 4.3% to 45% by volume). OSHA (Occupational Safety and Health Administration) regulations consider concentrations of 100 ppm $H_2S$ "immediately dangerous to life and health", while concentrations greater than 700 ppm lead to immediate death. NIOSH (National Institute for Occupational Health) recommends the maximum exposure of humans to $H_2S$ to not exceed 10 ppmv for 10 minutes. HF and HBr have OSHA permissible exposure limits of 3 ppmv while the limits for HCN, $PH_3$, $AsH_3$, and $NH_3$ are 10 ppmv, 0.3 ppmv, 0.05 ppmv, and 50 ppmv, respectively. These gases are common byproducts of many industrial petrochemical processes including ethylene, propylene, Teflon™, polyvinyl chloride (PVC), nylon, viscose rayon production, and rubber production, as well as of de-sulfurization of natural gas and crude oil. Trace amounts as low as several ppbv to a few ppmv of these chemicals can seriously impede the respective chemical processes and lead to defective plastics and other products.

Hydrogen sulfide also occurs naturally in natural gas, oil, sewage and landfills. Its release to the environment, or incineration forming and releasing $SO_2$, even in small quantities, needs to be prevented. This requires sensitive detection of $H_2S$ in pipelines, petrochemical processes and in and around facilities dealing with this gas. Rising world wide energy demand and energy prices have driven an increasing use of crude oil and natural gas with very high $H_2S$ concentrations which places ever rising demands on $H_2S$ removal technologies and reliable, accurate, and sensitive detection of $H_2S$.

Natural gas is an important energy source for industry and personal homes because of its low cost and widespread availability. Unpurified natural gas can contain up to 60% hydrogen sulfide. Even less than 4 ppmv amounts of $H_2S$ can lead to corrosion of delivery pipelines, over time, potentially resulting in serious explosion and leakage hazards while necessitating costly replacement of segments of the pipeline. For reference, downtime for natural gas pipelines can cost upwards of several thousand dollars per second. Hydrogen sulfide must be removed from natural gas to prevent pipeline corrosion and the emission of another toxic gas, $SO_2$, which is created during burning. Sensitive, real time detection of hydrogen sulfide in natural gas is becoming increasingly more important to facilitate limiting concentrations to below the 4 ppm tariff level.

Additional concerns with $H_2S$ in gas streams can arise due to its tendency to degrade or poison catalysts in chemical processes. Such poisoning can occur due to deposition of surface sulfur on the metal components of a catalyst body and the substitution of sulfur ions for oxygen ions near the surface of metal oxides. In other cases, sulfur can chemically substitute for oxygen in the surface oxides of a catalyst, thereby creating metal sulfides with reduced activity.

Refinery fuel gas is an important energy source for petrochemical processing plants, generating energy from combustible waste gases which occur as byproduct of petrochemical processes, including production of ethylene, propylene and iso-butane, which are the fundamental building blocks for all types of plastics. U.S. Environmental Protection Agency regulations limit hydrogen sulfide levels in fuel gas to less than 160 ppm for emission of $H_2S$ and $SO_2$. Also, the presence of $NH_3$ in fuel gas can lead to formation and emission of environmentally incompatible nitrous oxides during combustion.

Conventional techniques for measuring reactive gases rely primarily on the use of chemical sensors such as lead acetate tape, broadband non dispersive UV photometry, gas chromatographs (GC) or small surface area electro-chemical sensors, such as metal-oxide semiconductors. These techniques have generally proven unsuitable for on-line or at-line real time process control and real time hazard prevention. Drifting calibration, slowness of measurement, sensor saturation, long recovery times after sensor saturation and sensor element degradation from contaminants in the background gas typically lead to erroneous readings and can lead to harmful emissions or a failure to detect hazardous or unacceptably high concentrations of reactive gases to go undetected. Such conventional sensors tend to be quite maintenance intensive, requiring frequent replacement of costly consumables such as lamps, GC columns, carrier gas for GCs, lead acetate tape or aqueous ammonia solution. In addition, lead acetate tape analyzers create significant amounts of hazardous, lead containing waste. Analyzers relying upon indirect, UV detection of $H_2S$ create di-ammonium sulfide, $(NH_4)_2S$, waste which can easily release $H_2S$ again. Additional limitations can arise from electrochemical sensors' abilities to interact with only a very small portion of the gas environment, directly at the location of the sensor element itself. This can potentially lead to mischaracterization of harmful concentrations, particularly in a less than ideally mixed gas stream. Conventional sensors also tend to be highly sensitive to condensable contaminants in the background gas stream which can cause erroneous readings and earlier than expected sensor failure.

Gas chromatographs (GCs) are being used, generally delivering accurate results albeit at very high initial, system and infra structure cost, high consumables cost for carrier gas and separation columns and high ongoing maintenance cost, providing measurement cycle times in the order of several minutes. This approach is generally too slow and does not allow real time process control feedback and detection that can effectively be used to prevent or reduce harmful $H_2S$ concentrations, particularly in gas streams with rapidly varying compositions.

Attempts have been made to measure $H_2S$ and other reactive gas concentrations by means of ultraviolet light absorption spectroscopy, using a spectrally broad ultraviolet lamp and a diffraction grating. The continuum-like absorption spectrum of, for example, $H_2S$ in the ultraviolet can cause erroneous, ambiguous readings and limited repeatability of measurement, especially in interfering background gas streams, making it unsuitable for precise, real time process control and hazard prevention. To overcome this potential ambiguity of direct UV based $H_2S$ concentration measurement, some non dispersive, broadband UV instruments attempt to indirectly determine $H_2S$ concentration by converting $H_2S$ into $(NH_4)_2S$ and photometrically measuring $(NH_4)_2S$. This technique heavily relies upon the assumption that the chemical reaction to $(NH_4)_2S$ is complete, without aging effects and temperature influence. Another instrument combines the non-dispersive UV absorption technique with gas chromatography columns to separate $H_2S$ from the remainder of the gas stream, suffering from the same inadequacies as a GC.

HCl, HF, HBr, $AsH_3$, and $NH_3$ are also common in a variety of industrial and petrochemical processes and applications, either as chemical process byproducts or in feed streams. HCl, HBr, and HF are corrosive gases, particularly in the presence of any moisture. Among other possible sources, they can be used in various applications for production of plastics and polymers, including PVC, Teflon and nylon, and can also be byproducts of petroleum cracking, especially in alkylation processes. Ammonia is a caustic gas with a characteristic pungent odor that often serves as a precursor to foodstuffs and fertilizers and some pharmaceuticals. Arsine and phosphine have proven detrimental to polymerization reactions, which create the plastic feed stock, even in very low ppb level concentrations. Various wet chemical detection techniques or specialized gas chromatographs are available for quantifying HCl, HBr, HF, HCN, $AsH_3$, $PH_3$, and $NH_3$, but like $H_2S$, real time, accurate, robust, and low maintenance detection and quantification methods for use in industrial processes have been lacking.

SUMMARY

In a first implementation, a method includes determining a first measured concentration of a reactive gas in a first sample of a gas mixture. The gas mixture includes the reactive gas at a reactive gas concentration and a first background composition that contributes spectral interference that hampers direct spectroscopic measurement of the reactive gas concentration in the gas mixture. The first measured concentration is determined by generating a first differential absorption spectrum by subtracting a first background absorption data set from a first sample absorption data set collected for the first sample and converting the first differential absorption spectrum to a first measured concentration of the reactive gas in the gas mixture using calibration data. The first background absorption data set includes data characteristic of absorption characteristics of the first background composition. A selection is made whether to use the first background absorption data set or a second background absorption data set to determine a second measured concentration of the reactive gas in a second sample of the gas mixture based on whether a correlation of the first background absorption data set to the first background composition is within a pre-defined tolerance. The second measured concentration is determined by generating a second differential absorption spectrum by subtracting either the first background absorption data set or the second background absorption data set from a second sample absorption data set for a second sample of the gas mixture and converting the first differential absorption spectrum to the second measured concentration of the reactive gas in the gas mixture using the calibration data.

In a second implementation, a system can include a wavelength scannable laser operating in a scan range that includes a target wavelength, a detector positioned to receive and quantify light intensity from the scannable laser, a sample cell having an interior volume disposed such that light from the tunable diode laser passes through at least part of the interior volume before the light is received by the detector, a memory that includes or stores a background absorption data set and calibration data, and a processor. The processor controls the tunable diode laser and receives a sample absorption data set from the detector. The sample absorption data set is collected for a gas mixture in the interior volume. The gas mixture includes a reactive gas and a background composition that contributes spectral interference that hampers direct spectroscopic measurement of the reactive gas concentration in the gas mixture. The processor generates a differential absorption spectrum for each sample absorption data set by subtracting the background absorption data set from the sample absorption data set and converts the differential absorption spectrum to a measured concentration of the reactive gas in the gas mixture using calibration data. The processor further determines whether the background composition has substantially changed relative to the background absorption data set by analyzing the differential absorption spectrum and switching to a new background absorption data set if the background composition has substantially changed.

In optional variations, one or more of the following additional features can be included. A second background absorption data set can be used that differs from the first background absorption data set to generate the second differential absorption spectrum if the first background composition has a substantially different absorption profile relative to the first background absorption data set. A second background absorption data set that is identical to the first background absorption data set can be used to generate the second differential absorption spectrum if the first background composition has a substantially similar absorption profile relative to the first background absorption data set.

The first differential absorption spectrum can include a first region with a first spectral response characteristic of the concentration of the reactive gas and a second region with a second spectral response characteristic of a correlation between the first background composition and the first background absorption data set. The first region and the second region would not substantially overlap, and the determining can include comparing the correlation to a predetermined threshold. The first region can optionally include wavelengths within approximately ±1 cm-1 of the target wavelength. The first sample absorption data set can be collected using a scannable laser source operating in a scan range that includes the target wavelength. The scannable laser source can optionally include a tunable diode laser or a quantum cascade laser.

The background absorption data set can optionally be collected for a background sample prepared from the gas mixture using the scannable laser in the scan range. The preparing of the background sample can optionally include treating a volume of the gas mixture to reduce a concentration of the reactive gas without substantially altering the background composition in the background sample. The treating of the gas mixture can optionally include passing the gas mixture through a scrubber material that converts molecules of the reactive gas to a non-gaseous state. The scrubber material can optionally include one or more of metal oxides, cupric dicarbonate, solid and liquid-phase inorganic and organic acids and bases, metal oxide and copper oxide nano particles suspended on larger grain size carrier particles, solid state scrubbers, liquid scrubbers, amine solutions, aqueous ammonia solutions, and aqueous solutions of strong acids or bases. The first sample absorption data set and the first background absorption data set can include be collected alternately in a single sample cell. Alternatively, the first and second sample absorption data sets and the first and second background absorption data set can optionally be recorded in a sample cell and a background sample cell, respectively, with substantially identical optical path lengths.

The first and the second background absorption data sets can optionally include empirically obtained historical absorption data for a first and a second characteristic background composition. The reactive gas can optionally be selected from a group consisting of hydrogen sulfide, hydrogen chloride, hydrogen fluoride, hydrogen bromide, hydrogen cyanide, arsine, phosphine and ammonia and the target wavelength is one at which the reactive gas has an absorbance selected according to a figure of merit greater than $1 \times 10^{-6}$. The background composition can optionally include one or more of a group consisting of natural gas, alkanes, refrigerants, olefins, hydrogen, nitrogen, oxygen, chlorine, carbon dioxide, ammonia, water, carbon monoxide, hydrocarbons, hydro-fluorocarbons, hydro-chlorocarbons, and hydrofluorochlorocarbons. The scan range can optionally include wavelengths within approximately ±2 cm-1 or less of the target wavelength.

Articles are also described that comprise a tangibly embodied machine-readable medium operable to cause one or more machines (e.g., computers, etc.) to result in operations described herein. Similarly, computer systems are also described that can include a processor and a memory coupled to the processor. The memory can include one or more programs that cause the processor to perform one or more of the operations described herein.

The subject matter described herein provides many advantages. Optical absorption spectroscopy can be used to detect reactive gases, including but not limited to $H_2S$, HCl, HF, HBr, HCN, $AsH_3$, $PH_3$ and $NH_3$. Light from a source such as a laser or any other suitable, spectrally narrow light source is detected by a detector after passing through a gas sample. By monitoring the amount of light absorbed by the sample, at specific wavelengths, the concentration of the target gas can be accurately determined. Among other possible benefits, improved signal to noise ratio and lowered minimum detection limits can be achieved by reducing system background noise, such as that originating from electronic circuitry, optical fringes, ambient noise and laser noise, by combining 2f wavelength modulation spectroscopy and phase sensitive lock-in amplification with differential spectroscopy.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed embodiments. In the drawings.

DETAILED DESCRIPTION

Figure 1:
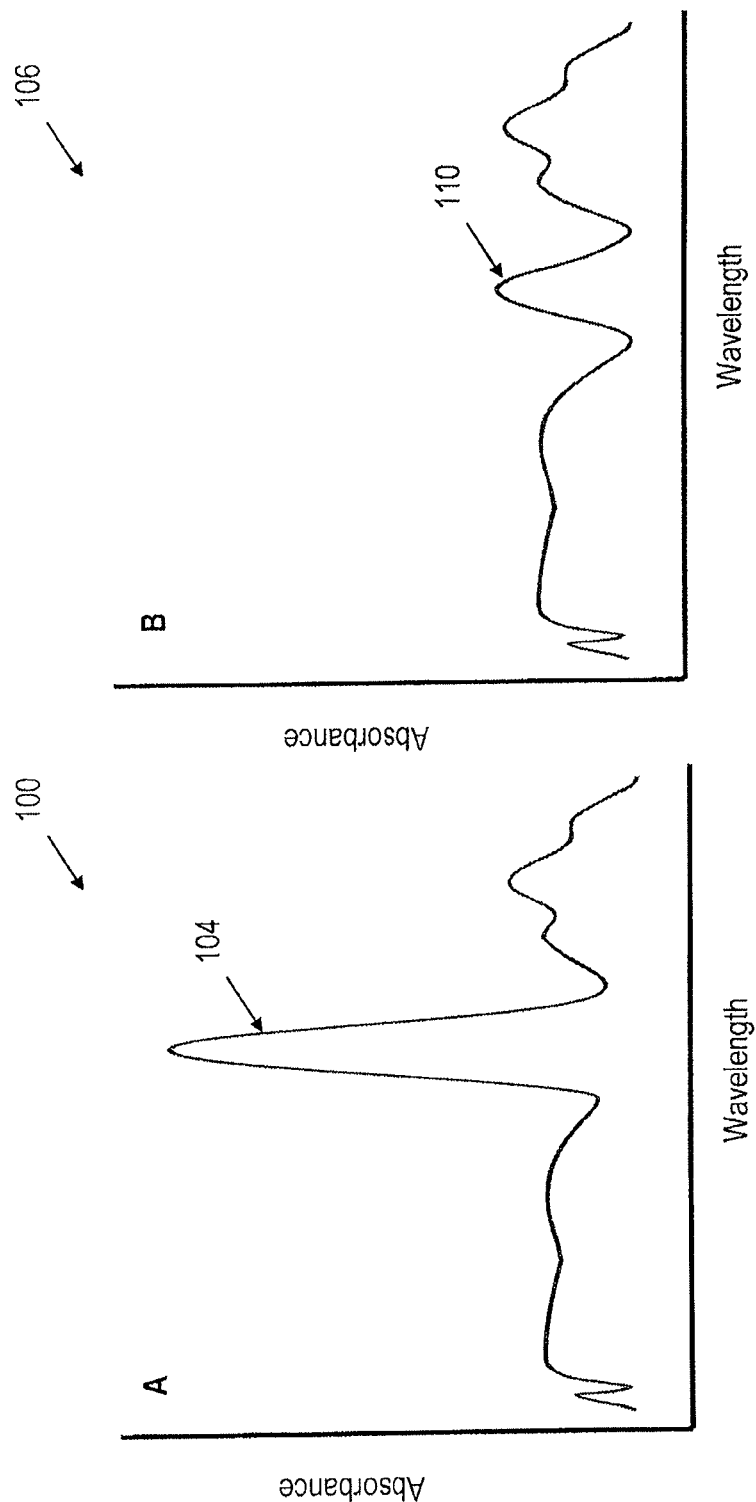
FIG. 1A and FIG. 1B are charts showing sample absorbance spectra for a complex gas mixture containing a reactive gas with and without scrubbing.

The subject matter described herein relates to the detection of trace amounts of reactive gases, such as for example $H_2S$, HCl, HF, HBr, HCN, $AsH_3$, and $NH_3$, in various infrared absorbing background gases and mixtures of those gases, including, but not limited to, methane, ethane, propane, pentane, hexane, ethylene, propylene, iso-butane, ambient air, nitrogen, oxygen, hydrogen, CO, $CO_2$, chlorine, fluoro-carbons, chloro-carbons, chloro-fluoro-carbons, natural gas and refinery fuel gas, and other non-infrared absorbing gases such as noble gases, $O_2$, $N_2$, $H_2$, and $Cl_2$. Sensitive detection of reactive gases like $H_2S$, HCl, HF, HBr, HCN, $AsH_3$, $PH_3$ and $NH_3$ in the environment, inside petrochemical production, natural gas pipelines and processes such as Claus de-sulfurization plants and waste incinerators is important to prevent occupational, environmental and industrial safety hazards, harmful accidents and costly repairs, especially of pipelines used for transportation of natural gas and petrochemical process gases.

A common challenge with optical absorption spectroscopy arises from the fact that multiple constituents in a sample can absorb at substantially the same wavelength over wide spectral ranges. This is especially true for low concentrations of reactive gases such as $H_2S$, HCl, HF, HBr, HCN, $AsH_3$, $PH_3$ and $NH_3$ in a background of hydrocarbon and fluoro- or chloro-carbon gases. As an example, natural gas used for burning, which is typically composed of greater than 80% methane ($CH_4$), contains hydrogen sulfide at typically less than 4 ppmv, as per distribution tariff. Refinery fuel gas, which can contain between 30% and 60% methane and other hydrocarbon gases, has to maintain $H_2S$ concentration at less than 160 ppmv to comply with EPA and other emission regulations. Conventional, spectrally broad spectroscopic methods (i.e., non-laser based) are generally not suitable for measurement of hydrogen sulfide in a $CH_4$ or hydrocarbon gas background because the absorption by $CH_4$, and other hydrocarbon gases which are present in much larger quantities, completely obscures the much weaker absorption by $H_2S$ at all wavelengths in the visible and infrared region. Similar overlap can be observed for other reactive gases such as for example HCl, HF, HBr, HCN, $AsH_3$, $PH_3$ and $NH_3$. This type of spectral overshadowing of the target analyte absorption can occur with substantially all hydro-, fluoro, and chlorocarbon gases, including but not limited to methane, ethane, propane, butanes, pentanes, hexanes, septane, octane, nonane, decane, ethylene, propylene, iso-butane and mixtures thereof.

In one implementation, sensitive reactive gas detection can be achieved by overcoming spectral overshadowing of one or more reactive gas absorption lines by the background gas using differential tunable diode laser (D-TDL) absorption spectroscopy. Laser absorption of a gas stream or sample is measured in a scan range that includes the wavelength of a selected reactive gas absorption line to generate a sample absorption data set. A background absorption data set is subtracted from the sample absorption data set to generate a differential absorption spectrum from which the reactive gas concentration can be obtained using calibration data from one or more predetermined calibration values.

The background absorption data set can in some implementations be one of a group of background absorption data sets that are pre-loaded in a memory that is accessible by a processor that converts the absorption data to concentration values. In these implementations, a background data set that is expected to be most representative of the actual background composition of the gas mixture is selected.

In other implementations, a background absorption data set can be generated in real or near-real time by treating a sample of the gas mixture to reduce the reactive gas concentration while leaving the background composition of the gas mixture substantially unchanged. This treating can be accomplished in some examples by passing a sample volume of the gas mixture through a scrubber device that contains a material that preferentially reacts with the reactive gas to substantially convert the reactive gas to a non-gaseous state. Laser absorption of the background sample is measured in the same scan range that includes the wavelength of the selected reactive gas absorption line to generate a background sample absorption data set. In this manner, the background composition of the gas mixture that contributes spectral interference is directly measured and accounted for in the differential absorption spectrum, thereby permitting accurate extraction of the spectral response attributable to the reactive gas even in gas mixtures with dynamically variable background compositions.

A new background sample can be prepared and analyzed periodically based on a preset or user selectable interval, continuously in parallel with an unscrubbed sample, or via an automated initiation process via which the differential absorption spectrum is analyzed to ascertain whether the current background absorption data set adequately characterizes the current background composition of the gas mixture. This automatic initiation is discussed in greater detail below.

The scrubber material can be selected from a range of options, including but not limited to metal oxides, cupric dicarbonate, liquid and solid inorganic and organic acids and bases, solid state scrubbers, liquid scrubbers, amine solutions, aqueous ammonia solutions, and aqueous solutions of strong acids or bases. In some implementations, the scrubber material can include metal oxide nano particles, such as for example copper oxide nano particles that are suspended on larger grain size carrier particles. Examples of this scrubber material are discussed in greater detail in co-pending and co-owned provisional application for U.S. patent No. 60/968, 846, the disclosure of which is incorporated by reference herein.

FIG. 1A and FIG. 1B show graphs of absorbance vs. wavelength for two complex gas mixtures. The first gas mixture, whose absorbance spectrum 102 is shown in FIG. 1A, contains hydrogen sulfide in addition to a background composition that contains one or more gases with absorbance features that might interfere with spectral analysis of hydrogen sulfide. A substantial absorption peak 104 corresponds to a hydrogen sulfide absorption feature. The second gas mixture, whose absorbance spectrum 106 is shown in FIG. 1B is identical to that of the first gas mixture with the exception of the hydrogen sulfide which has been removed or at least substantially reduced in concentration. Although the peak 110 corresponding to the location of the hydrogen sulfide peak 104 in FIG. 1A is not as pronounced, substantial absorption nonetheless remains. Particularly in hydrocarbon mixtures with varying composition, the strength of this interfering absorbance can be significant and non-constant and therefore quite difficult to correct for via conventional differential spectroscopy methods.

In various implementations, the current subject matter can be used to accurately measure reactive gas concentrations in gas mixtures having background compositions that include infrared absorbing gases and any mixture thereof, including but not limited to natural gas, methane, ethane, propane, butanes, hexanes, septane, octane, nonane, decane, ethylene, propylene, iso-butane, fluorocarbons, chlorocarbons, fluorochlorocarbons, CO, $CO_2$, and $H_2O$. The background composition can also include gases which do not absorb in the infrared, including but not limited to noble gases, $O_2$, $N_2$, $H_2$ and $Cl_2$.

Figure 2:
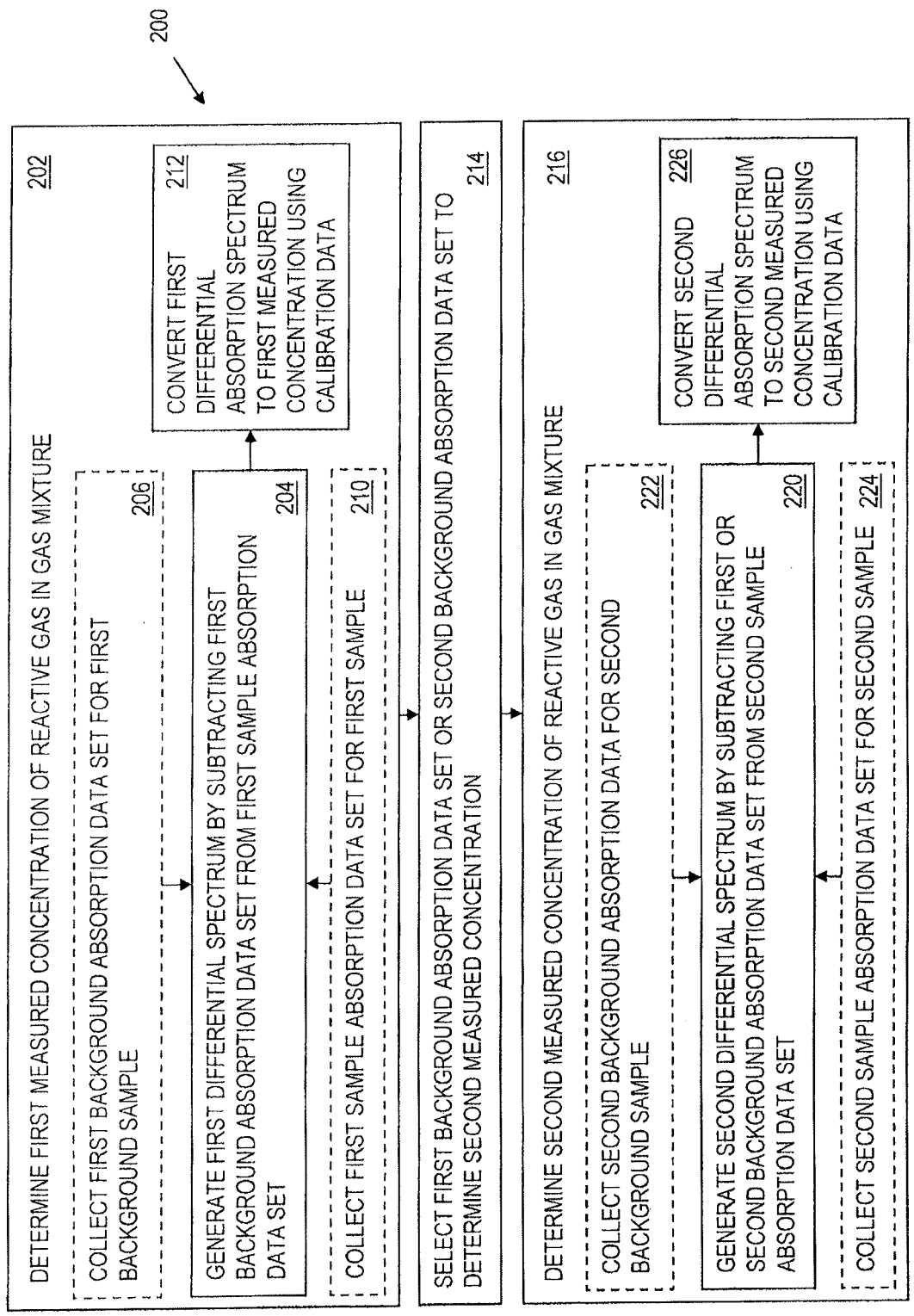
FIG. 2 is a process flow diagram illustrating a method for determining reactive gas concentrations in complex backgrounds.

FIG. 2 is a process flow chart 200 describing a method that can be used in some implementations to accurately quantify reactive gas concentrations in a gas mixture having a dynamic, complex background composition. At 202, a first measured concentration of a reactive gas in a first sample of a gas mixture that contains a first background composition is determined by generating first differential absorption spectrum at 204. The first differential absorption spectrum can be generated by subtracting a first background absorption data set from a first sample absorption data set. The method can optionally include collecting the first background absorption data set for a first background sample at 206 and collecting the first sample absorption data set for a first sample at 210. The first background sample includes data that are characteristic of the absorption characteristics of the first background composition. At 212, the first differential absorption spectrum is converted to the first measured reactive gas concentration using calibration data. The calibration data can be obtained by analyzing one or more standard samples having a known concentration of the reactive gas or gases of interest and quantifying the differential spectral response for the standard sample or samples. In some implementations, standard samples with different background compositions can be used to improve accuracy of the measured reactive gas concentrations. Other types of calibration data could also be used.

Figure 3:
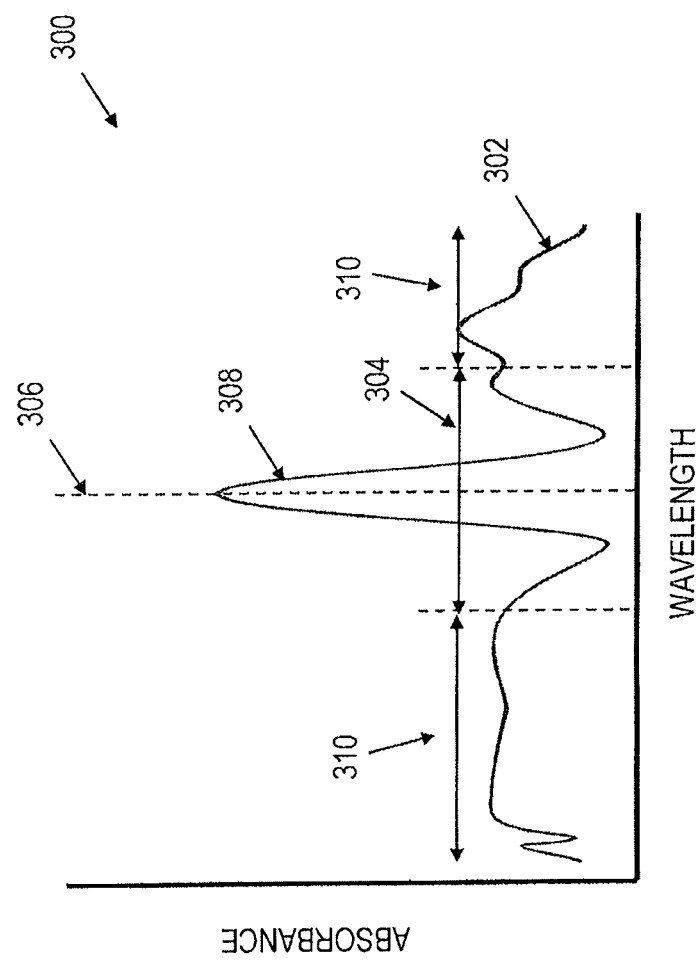
FIG. 3 is a chart showing a sample differential spectrum for a reactive gas in a complex gas mixture.

Based on an analysis of the first differential absorption spectrum, a selection is made at 214 whether to use the first background absorption data set for the next sample or to switch to a second background absorption data set. This selection can in some implementations include analyzing a second region of the first differential absorption spectrum that is distinct from a first region of the first differential absorption spectrum in which a substantial reactive gas absorption feature occurs. FIG. 3 shows a chart 300 of a differential absorption spectrum 302 resulting from the subtraction of the absorption curve of FIG. 1B from that of FIG. 1A. In one example, the first region 304 might be the part of the first differential absorption spectrum lying within a range of ±1 cm$^{-1}$ on either side of the target wavelength 306 which can at least partially coincide with a substantial absorption feature 308 of the reactive gas of interest. The second region 310 could be the remainder of the first differential absorption spectrum. The second region 310 can optionally be analyzed to determine how well the first background absorption data set represents the actual absorption due to the first background composition. This can be accomplished using one of a number of mathematical correlation functions or the like. In effect, this process examines how well subtraction of the first background absorption data set from the first sample absorption data set leads to a constant observed absorption in the second region of the first differential absorption spectrum. If the resulting first differential absorption spectrum is not substantially constant in the second region, this can be taken as an indication that the background composition of the gas mixture has changed relative to the characterization of the background composition that is presented by the first background absorption data set.

Continuing with FIG. 2, a second measured concentration of the reactive gas in a second sample of the gas mixture that contains a second background composition is determined by generating first differential absorption spectrum at 216. The second differential absorption spectrum can be generated by subtracting a second background absorption data set from a second sample absorption data set at 220. The method can optionally include collecting the second background absorption data set for a second background sample at 222 (if a second background absorption data set is determined to have been needed at 214) and collecting the second sample absorption data set for a second sample at 224. The second background sample data set includes data that are characteristic of the absorption characteristics of the second background composition. At 226, the second differential absorption spectrum is converted to the second measured reactive gas concentration using the calibration data.

The background sample data sets discussed above can be generated in real or near real time one of the systems discussed below or some other configuration that allows a reproducible measurement of a gas mixture both with and without the reactive gas of interest. In some optional implementations, a background sample is collected periodically at some preset interval to routinely verify that the background composition of the gas mixture is well characterized by the background data set being used to generate the differential absorption spectrum for a given sample. This periodic feature can be used either in conjunction with the automated system described above or as a stand alone feature in which there is no automated process for determining if a new background data set is needed. In other implementations, a live background data set is not collected. Instead an archived background absorption data set is used based on one or more measurable characteristics of the gas mixture. For example, the background composition of a natural gas stream could be periodically determined using a gas chromatograph, and a background absorption data set collected for a sample having the identified composition can be used.

Alternatively, the background sample absorption data set can be selected based on a known process stream, based on real time measurements of a single component of the gas mixture that is used as a surrogate for the overall gas mixture composition. These same methods could be also be used to identify when a new real time or near real time measurement of the background composition should be performed. Other methods and systems for identifying a most representative background data set from an archive and/or determining that a new background sample should be analyzed can also be used. For example, in implementations where the second background absorption data set is selected 214 from an archive of historical or empirically generated background data sets, the new background absorption data set can optionally be selected using the first sample absorption data set to generate one or more test differential absorption spectra with one or more candidate archived background absorption data sets. The candidate background sample absorption data set that generates a test differential absorption spectrum showing the best correlation in the second region can be selected as the second background sample absorption data set.

Figure 4:
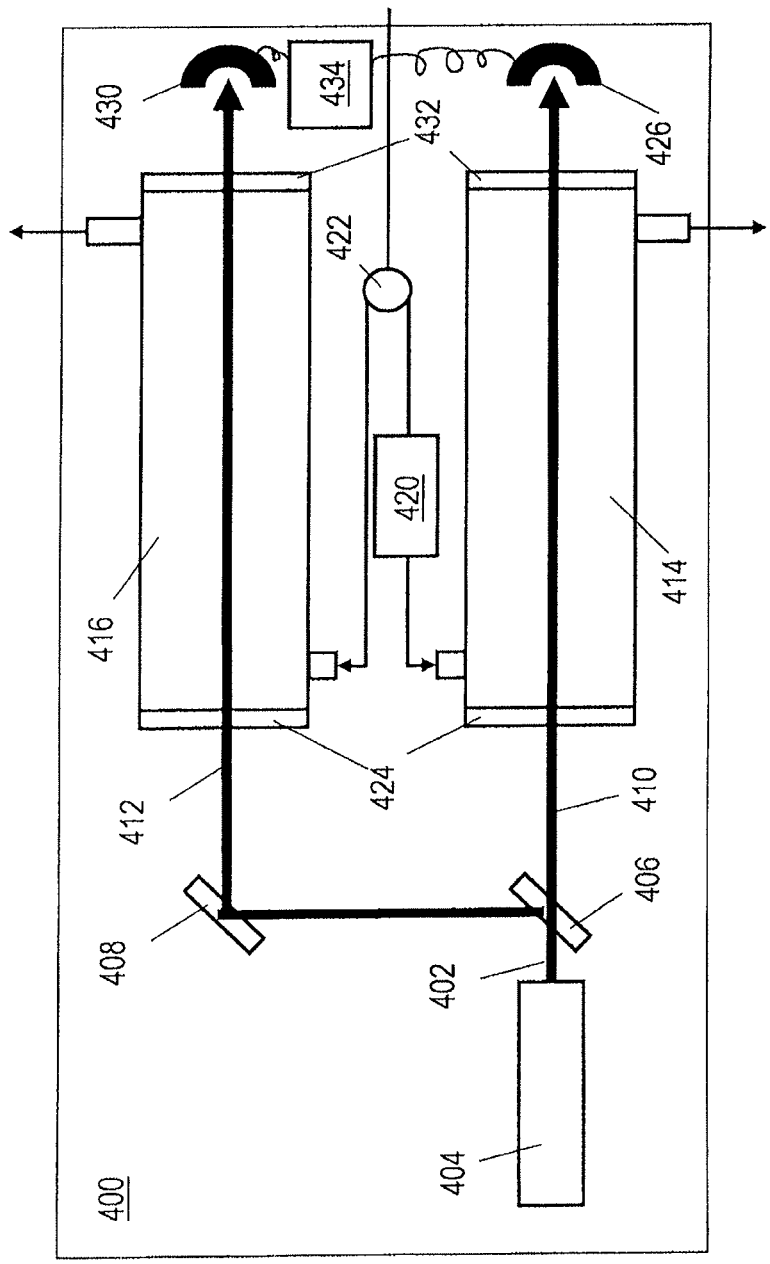
FIG. 4 is a schematic diagram illustrating a first system for analyzing reactive gas concentrations in complex gas mixtures.
Figure 5:
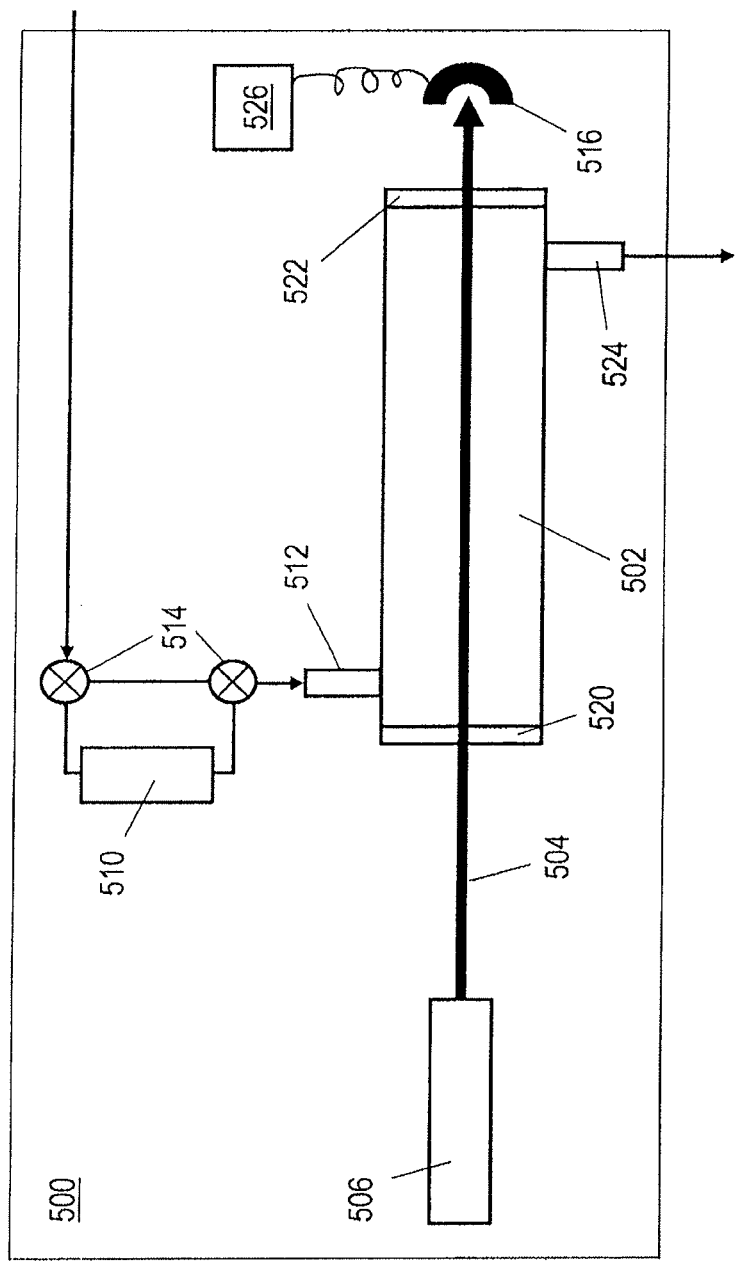
FIG. 5 is a schematic diagram illustrating a second system for analyzing reactive gas concentrations in complex gas mixtures.

FIG. 4 and FIG. 5 illustrate sample analyzers that can be used to detect and quantify reactive gas concentrations in gas mixtures with complex background compositions. FIG. 4 depicts an analyzer 400 with a dual beam arrangement in which the beam 402 from the light source 404 is split by a beam splitter 406 and mirror 408 into a first beam 410 and a second beam 412 that passes through gas held in a first 414 and a second 416 sample cell, respectively. The first sample cell 414 contains a first sample of the gas mixture that is treated to be a background sample as referred to in FIG. 2. The background sample can be prepared by removing or reducing the reactive gas concentration (for convenience, the process of reducing the concentration of the reactive gas is referred to as "scrubbing" for purposes of this document). The second sample cell 416 contains a second sample of the gas mixture that has not been scrubbed. FIG. 5 shows an alternative analyzer 500 with a single beam, single sample cell arrangement in which the first sample and the second sample alternatively and sequentially enter the sample cell 502 where they are illuminated by the beam 504 from the light source 506.

More specifically, with reference to the analyzer 400 shown in FIG. 4, the first beam 410 is directed through the first sample cell 414 containing the first sample which has been scrubbed by passing it through a scrubber 420. The second beam 412 is directed through a second sample cell 416 of identical optical path length to the first sample cell 414. The second sample cell 416 contains the second sample which has not been scrubbed. As such, the second sample contains components found in the first sample (e.g. the background sample) in addition to the reactive gas at the concentration present in the gas mixture. In operation, gas flowing into the analyzer 400 is split between the two first 414 and the second 416 sample cells. This can be accomplished by a flow divider 422 or other equivalent apparatus for dividing gas flow between two channels. Gas flowing to the second sample cell 416 passes through the scrubber 420 that reduces the reactive gas concentration from the gas mixture to produce the first sample that is the background sample.

The scrubber 420 can be any device or process that reduces the concentration of the reactive gas in the gas mixture, including but not limited to those mentioned above. The scrubber 420 is advantageously chosen to not substantially affect the concentration of the other components of the gas mixture by more than 5% by volume. Gas flowing to the second sample cell 416 does not pass through the scrubber 420.

The first 410 and second 412 split beams pass into the first 414 and second 416 sample cells respectively. Depending on the configuration of the analyzer 400, the incident light can pass through first windows 424 as shown in FIG. 4. The gas in each sample cell can absorb some fraction of the beam intensity, and the first 410 and second 412 light beams then impinge upon a first 426 and a second 430 detector respectively. The first 426 and second 430 detectors can each be a device that quantifies an intensity of light that is incident on a surface or aperture of the detector. In some implementations, the detector 426, 430 can be, photodetectors, including but not limited to an Indium gallium arsenide (InGaAs) indium arsenide (InAs), silicon (Si), germanium (Ge) photodiode, a mercury-cadmium-telluride (MCT), lead-sulfide (PbS) photodetector, or another photodetector which is sensitive to light in the 400 to 50000 nm wavelength regions). Depending on the configuration the beams can pass through second windows 432 to exit the first and second sample cells. The example illustrated in FIG. 4 depicts the first and second sample cells as single pass configurations in which the beams enter the respective sample cells through first windows 424, pass through the gas contained in each sample cell, and exit the respective sample cells through second windows 432. Other configurations are within the scope of the disclosure, as discussed below.

The first detector 426 quantifies the intensity of the first beam impinging upon it, and thus passing through the first sample cell 414, as a function of wavelength. Likewise, the second detector 430 quantifies the intensity of the second beam impinging upon it, and thus passing through the second sample cell 416, as a function of wavelength. In this manner, the first detector 426 quantifies the transmitted intensity for the first sample, in this example the scrubbed background sample, and the second detector 430 quantifies the transmitted intensity for the second sample, which has not been scrubbed. Data from the first detector 426 and the second detector 430 is passed to a control unit 434, such as for example a microprocessor, which records and/or processes data from the detector to generate a differential spectrum from which the reactive gas concentration in the second sample can be calculated. The concentration of the reactive gas is dependent on the mole fraction of reactive gas molecules as well as the temperature and pressure of the gas mixture being measured. As such, the temperature and pressure in the first 414 and second 416 sample cells can be monitored and/or controlled.

To account for detector drift and other potential measurement artifacts, some variations can periodically record an absorption spectrum for each sample cell with no gas to determine the detector's dark current "zero" or to periodically reverse the flows such that the first sample cell 414 is supplied with unscrubbed gas and the second sample cell is supplied with the scrubbed, background sample.

The light source 404 can, in some implementations, operate at a spectrally very narrow wavelength substantially corresponding to a reactive gas absorption line where minimal absorption occurs by the background composition of the gas mixture, thereby minimizing the effects of interference due to the extremely high spectral purity of the laser (narrow line width). The current system can incorporate a laser as its light source, emitting in the wavelength range between 400 nm and 20,000 nm. Tunable diode lasers emitting light within the wavelength range from 400 nm to 3000 nm can be utilized. In addition, quantum cascade lasers (such as those described by J. Faist, F. Carpasso, D. L. Sivco, A. L. Hutchinson, S, N. G. Chu, and A. Y. Cho, Appl. Phys. Lett. 72, 680 (1998), the contents of which are hereby incorporated by reference) emitting light in the wavelength range from 4000 nm to 20,000 nm can also be utilized. Alternately, the spectrally narrow light source can also be constructed by nonlinear difference and sum frequency mixing of suitable lasers. However, nonlinear frequency mixing can be optically complex and too expensive for practical commercial applications. Alternatively, a color center laser can be utilized, but such lasers are not always suitable for use in commercial field instrumentation due to their relatively large physical size, high power consumption, high maintenance requirements, need for cryogenic cooling, and cost.

The light source 404 can optionally be a single frequency diode laser or other light source that emits at the target wavelength and that is scannable over a frequency or wavelength range in which the target wavelength is found. Illustrative examples of target wavelengths are disclosed below. Other wavelengths where the reactive gas molecule has a strong absorption line and the interference absorptions from other gas species in the background composition of the gas mixture, such as for example $CH_4$, $H_2O$ and $CO_2$, are relatively weaker can also be used. Alternatively the light source 404 can optionally be a quantum cascade laser, or the like. In some variations, the wavelength of a tunable diode laser light source 404 can be scanned across the reactive gas absorption feature by varying the injection current while keeping the laser temperature constant. The laser temperature can in some implementations be controlled by placing the laser in intimate contact with a thermoelectric cooler (Peltier cooler) whose temperature is measured with a thermistor and controlled by a feedback circuit.

Due to the removal of the reactive gas in the background sample, the light source 404 can operate at any reactive gas absorption line wavelength between 400 nm and 20,000 nm. In one implementation, lasers in the economically advantageous telecommunications wavelength band between 1500 nm and 1610 nm, including but not limited to 1567 nm, 1569.9 nm, 1574.5 nm, 1576.3 nm, 1578.1 nm, 1581.3 nm, 1582.1 nm, 1589.2 nm, 1589.8 nm, 1590 nm, and 1601.3 nm can be utilized for analysis of $H_2S$.

FIG. 5 depicts an analyzer 500 with a single-beam arrangement. A first sample that has been scrubbed and a second, non-scrubbed sample are alternately illuminated by the beam 504 from the light source 506 (which can have the same characteristics as light source 404 in FIG. 4) in a sample cell 502. Spectra are recorded individually for the first sample, which is the scrubbed background sample, and the second sample, which is not scrubbed. For a flow system, this process can be performed continuously and sequentially for multiple samples and multiple background samples. The analyzer 500 in FIG. 5 includes a scrubber 510 that can be placed in series with the gas inlet 512 to the sample cell 502 by, for example a pair of multi-way valves 514 which can optionally be solenoid valves or pneumatically operated valves. As noted above, the scrubber 510 can be any device or process that reduces the concentration of the reactive gas in a complex background. As with the system shown in FIG. 4, the scrubber 510 is advantageously chosen to not substantially affect the concentration of the other components of the sample gas mixture. The second sample is not passed through the scrubber 510 and as such retains the hydrogen sulfide concentration that is present in the gas being measured.

In operation of the analyzer 500 shown in FIG. 5, gas is alternatively conveyed to the sample cell inlet 512 either directly or via the scrubber 510 by appropriate operation of the two way valves 514. The detector 516 quantifies the intensity of the beam 504 impinging upon it, and thus passing through the sample cell 502, as a function of wavelength. Thus, when the first sample, which passes through the scrubber to reduce its reactive gas concentration, is in the sample cell 502 the detector 516 quantifies the transmitted intensity for the first sample, in this example the scrubbed background or reference gas. The detector 516 quantifies the transmitted intensity for the second sample, containing the original reactive gas concentration, when gas flows directly to the sample cell without passing through the scrubber 510.

The sample beam can optionally enter the sample cell through an input window 520 and exit the cell though an exit window 522. Alternative sample cell configurations, such as those discussed above in regards to FIG. 4, are also within the scope of this disclosure. Gas exits the sample cell 502 via the exhaust outlet 524. Intensity data from the detector 516 are passed to a data analysis device 526, such as for example a microprocessor. The data analysis device 526 records and/or processes data received from the detector for the first sample and the second sample to generate a differential spectrum from which the reactive gas concentration in the second sample can be calculated. The concentration of reactive gas is dependent on the mole fraction of hydrogen sulfide molecules as well as the temperature and pressure of the gas being measured. As such, the temperature and pressure in the sample cell 502 can be monitored and/or controlled.

As noted above, a first sample and a second, scrubbed sample of a gas are illuminated by a laser light source. The path length of the sample cell can be varied depending on the strength of the specific absorption line of interest or the magnitude of the difference between the absorption line of interest and interfering absorption lines from other gas species present. A cell of insufficient length can not provide sufficient sensitivity while one of excessive length can absorb the entirety of the incident light such that no measurable signal reaches the detector (a situation called saturation). Other aspects of a similar analyzer and related techniques are described in U.S. patent application Ser. No. 11/715,599, filed on Mar. 7, 2007, and entitled "Measuring Water Vapor in Hydrocarbons," the disclosure of which is incorporated herein by reference.

To achieve longer optical path lengths without the use of extremely long sample cells, sample cell configurations within the scope of this disclosure can also include the use of one or more mirrors or reflective or refractive optical elements to route the beam such that the beam passes through the sample contained in the sample cell two or more times. In such a multipass configuration, the beam can enter and exit the cell through the same window or through different windows. In some implementations, windowless sample cell configurations can be utilized in which, for example, the laser source and/or the detector are contained within the sample cell. In some variations, a Herriott cell is utilized to increase effective path length. Alternatively, the light path can be a straight line between light source and detector in an open environment or inside a transport pipe or container for the sample gas.

Spectral overshadowing of the reactive gas absorption lines by the background gas can be overcome by operating the measurement at low pressure. At reduced pressure, spectral line broadening effects diminish, leading to spectral sharpening of absorption lines of every species in the gas mix. Depending upon the background composition of the gas mixture, this reduces or eliminates spectral overlap between the reactive gas and the background components of the gas mixture, enabling sensitive reactive gas detection. Suitable lines can in some implementations fulfill a figure of merit (FOM) of $>1\times10^{-6}$, at the respective working pressure. The FOM is defined as the absorption of 1 ppmv of the reactive gas divided by the total background gas absorption at the chosen wavelength. Low pressure TDL can be used to enhance reactive gas detection in all infrared absorbing gases. Low pressure measurements can be combined with the afore described differential TDL technique to further enhance sensitivity and broaden applicability to background gas streams.

In some variations, the system measures reactive gas in symmetrically diatomic gases which exhibit no interfering infrared background absorption. Such diatomic gases include but are not limited to air, $O_2$, $H_2$, $N_2$, and $Cl_2$. For $H_2S$, HCl, HF, HBr, HCN, $AsH_3$, $PH_3$, and $NH_3$, nearly every absorption line between 400 nm and 20,000 nm fulfills the detection requirements. The system can also measures reactive gas in noble gases which exhibit no interfering infrared background absorption. Such noble gases include Ne, Ar, Kr, Xe and Rd. For these gases, every $H_2S$, HCl, HF, HBr, HCN, $AsH_3$, $PH_3$, and $NH_3$ absorption line between 400 nm and 20,000 nm fulfills the detection requirements.

For $H_2S$ detection in air or in CO, $CO_2$ or any other gases exhibiting infrared absorption, $H_2S$ absorption lines between 400 nm and 20,000 nm exhibiting minimum overlap with the background gas absorption are suitable. The specific absorption transitions for measurement of $H_2S$, HCl, HF, HCN, HBr, $AsH_3$, $PH_3$, and $NH_3$ in various background gases are summarized in Tables 1-8, respectively. However, it will be appreciated that other wavelength ranges can be utilized provided that the reactive gas molecules absorb light at a greater level than do background gas molecules. Line selection can be facilitated using a Figure of Merit (FOM), which is defined as the absorption of 1 ppmv of the reactive gas divided by the total background absorption. Reactive lines satisfying an FOM of $>1\times10^{-6}$ may be suitable for sensitive detection according to the current subject matter.

TABLE 1

Illustrative absorption transitions for measurement of $H_2S$ 1567.0 nm
1569.9 nm
1574.6 nm
1576.3 nm
1578.1 nm
1581.3 nm
1582.1 nm
1589.2 nm
1589.8 nm
1590.0 nm
1590.2 nm
1590.6 nm
1591.1 nm
1601.3 nm
1919.1 nm
1919.3 nm
1928.0 nm
1944.6 nm
2599.1 nm
2604.7 nm
2639.6 nm
2650.1 nm

TABLE 1-continued

Illustrative absorption transitions for measurement of $H_2S$ 3718.7 nm
3730.0 nm
4049.2 nm
4129.3 nm
7460.5 nm
7601.7 nm
7734.6 nm
7893.3 nm

TABLE 2

Illustrative absorption transitions for measurement of HCl 1727.0 nm
1730.2 nm
1733.9 nm
1737.9 nm
1742.4 nm
1747.2 nm
1752.5 nm
1777.8 nm
1785.2 nm
1793.0 nm
1801.2 nm
1810.0 nm
1819.1 nm
3335.4 nm
3354.6 nm
3374.6 nm
3395.7 nm
3417.8 nm
3440.9 nm
3490.3 nm
3516.6 nm
3544.1 nm
3572.8 nm
3602.6 nm

TABLE 3

Illustrative absorption transitions for measurement of HF 1264.3 nm
1268.3 nm
1273.0 nm
1278.1 nm
1283.9 nm
1297.1 nm
1304.5 nm
1312.6 nm
1321.3 nm
2395.8 nm
2413.8 nm
2433.1 nm
2453.8 nm
2475.9 nm
2499.4 nm
2550.8 nm
2578.8 nm
2608.5 nm

TABLE 4

Illustrative absorption transitions for measurement of HCN 1527.4 nm
1528.0 nm

TABLE 4-continued

Illustrative absorption transitions for measurement of HCN 1528.6 nm
1538.9 nm
1539.7 nm
1540.5 nm
1844.7 nm
1845.5 nm
1846.4 nm
1861.4 nm
1862.6 nm
1863.7 nm
2483.2 nm
2484.9 nm
2497.5 nm
2508.7 nm
2512.6 nm
2518.5 nm

TABLE 5

Illustrative absorption transitions for measurement of HBr 1337.6 nm
1339.1 nm
1341.0 nm
1342.8 nm
1345.1 nm
1360.4 nm
1953.9 nm
1957.8 nm
1962.0 nm
1966.9 nm
1972.0 nm
1977.1 nm
1995.8 nm
2002.8 nm
2010.3 nm
2018.4 nm
2026.5 nm
2035.2 nm

TABLE 6

Illustrative absorption transitions for measurement of $AsH_3$ 2162.1 nm
2165.8 nm
2168.6 nm
2172.4 nm
2176.4 nm
2192.2 nm
2201.7 nm
2215.4 nm
2220.0 nm
2227.3 nm
2818.4 nm
2826.5 nm
2851.5 nm
2889.5 nm
2900.1 nm
2920.6 nm
2952.3 nm
2975.1 nm
4555.4 nm
4582.8 nm
4597.4 nm
4625.9 nm
4641.3 nm
4702.3 nm
4800.4 nm
4814.9 nm TABLE 6-continued Illustrative absorption transitions
for measurement of $AsH_3$ 4833.2 nm
4851.9 nm
4870.8 nm
4890.2 nm

TABLE 7

Illustrative absorption transitions
for measurement of $PH_3$ 2366.2 nm
2369.5 nm
2373.0 nm
2376.4 nm
2380.0 nm
2383.8 nm
2400.3 nm
2424.8 nm
2427.1 nm
2432.0 nm
2436.9 nm
2438.4 nm
4163.4 nm
4187.7 nm
4201.7 nm
4215.2 nm
4226.0 nm
4241.2 nm
4301.1 nm
4311.1 nm
4342.2 nm
4386.8 nm
4405.0 nm
4431.9 nm

TABLE 8

Figure 6:
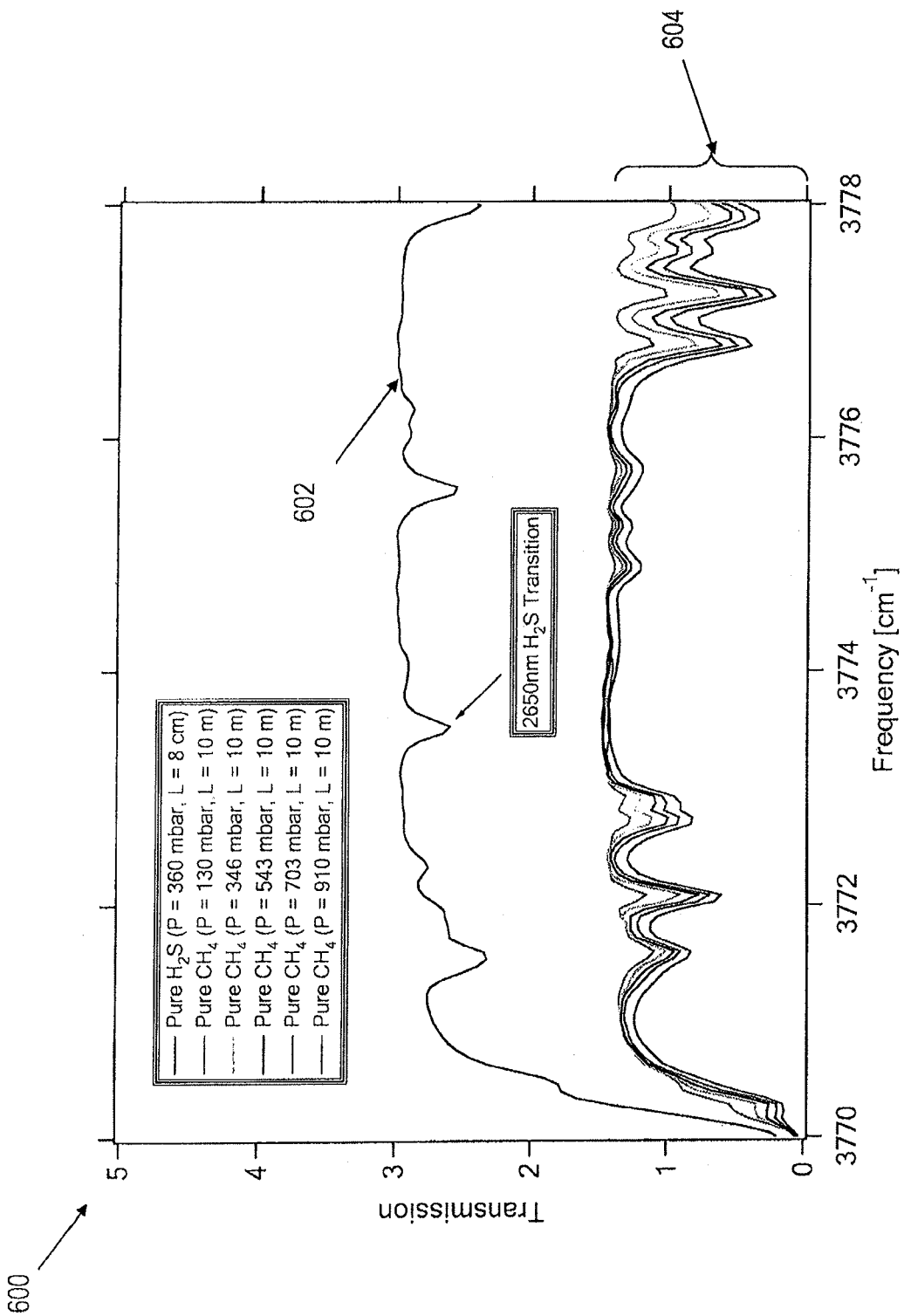
FIG. 6 is a chart showing transmission spectra of $H_2S$ and pure methane at different pressures with different absorption path lengths.
Figure 7:
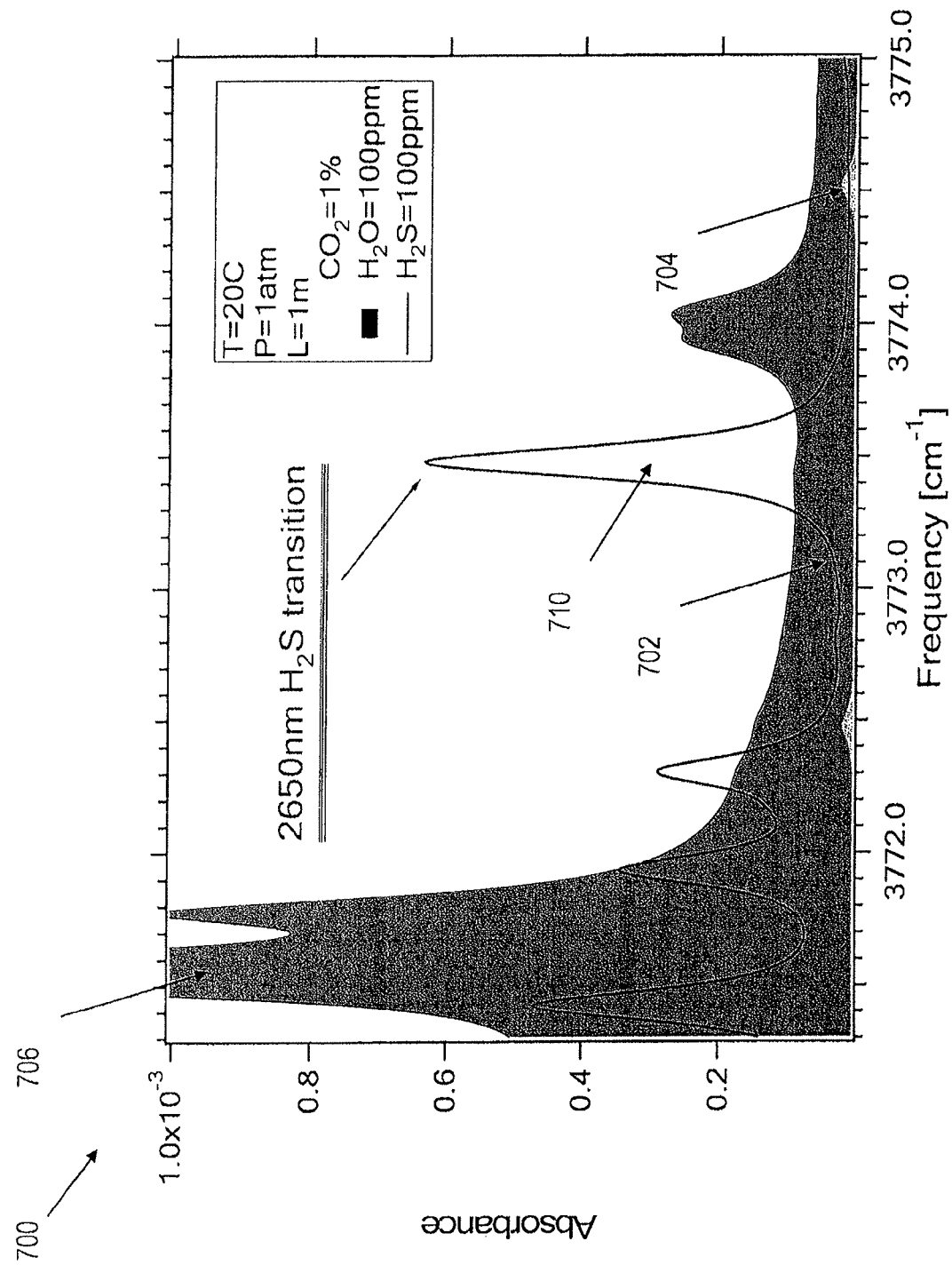
FIG. 7 is a chart showing absorption spectra of $H_2S$.

Illustrative absorption transitions
for measurement of $NH_3$ 1512.0 nm
1531.7 nm
1955.3 nm
1958.5 nm
1963.1 nm
1966.2 nm
1981.5 nm
1993.3 nm
1997.2 nm
2005.2 nm
2230.1 nm
2239.0 nm
2275.9 nm
2285.2 nm
2295.7 nm
2305.5 nm
2896.4 nm
2897.7 nm
2912.1 nm
2913.9 nm
2928.6 nm
2946.5 nm
2961.8 nm
2997.3 nm In various implementations, the current subject matter can be used to measure hydrogen sulfide in the near-infrared absorption bands, and more specifically, at wavelengths such as 1567 nm, 1569.9 nm, 1581.3 nm, 1582.1 nm, 1589.3 nm, 1589.6 nm, 1601.3 nm, 1944.6 nm, and 2650.1 nm, where absorption by methane and the infrared-absorbing constituents within air (the two main constituents being water and carbon dioxide) are weak. FIG. 6 is a transmission spectrum 600 of hydrogen sulfide 602 and pure methane 604 ranging from 3770 to 3778 $cm^{-1}$. 2. FIG. 7 is a graph 700 showing absorption spectra of $H_2S$ (100 ppm) 702, $CO_2$ (1%) 704 and $H_2O$ (100 ppm) 706. As can be seen, the hydrogen sulfide transition 710 at 2.650 um is well isolated from interference of methane, water and carbon dioxide, thereby allowing hydrogen sulfide to be measured in natural gas, hydrocarbon gas, fluorocarbon gas, hydro-fluorocarbon gas and other background gases.

In some variations, the current system employs harmonic spectroscopy. Harmonic spectroscopy as used in the current system involves the modulation of the TDL laser wavelength at a high frequency (kHz-MHz), detecting the signal at a multiple of the modulation frequency. Detection is performed at twice the modulation frequency, thus the teen second harmonic spectroscopy is used. Advantages to this technique include the minimization of 1/f noise, and the removal of the sloping baseline that is present in TDL spectra. The laser output power increases as the laser injection current increases, creating a sloping baseline for the light detected by the photodetector. Changing the laser injection current is how the laser is tuned across the absorption line.

In some implementations, direct absorption spectroscopy can be utilized. With such an arrangement, the laser frequency is tuned across the selected absorption transition and the zero-absorption baseline is typically obtained by fitting the regions outside the absorption line to a low-order polynomial. The integrated absorbance is directly proportional to absorbing species concentration as well as the line strength of the transition.

Cavity-ring down spectroscopy can also be utilized such that a pulsed or CW laser beam is injected into a cavity formed by at least one highly reflective mirrors or at least one optical element forming a resonant optical cavity by means of total internal reflection of the light beam. Trace level absorption of a target gas can be detected by utilizing the photon decay time inside this high-finesse optical cavity. In some variations, other cavity-enhanced spectroscopy (such as Integrated Cavity Output Spectroscopy (ICOS), Cavity Attenuated Phase Shift Spectroscopy (CAPS), Cavity Output Autocorrelation Spectroscopy (COAS)) will be employed.

Photoacoustic spectroscopy, which is based on the photoacoustic effect, can be utilized. Some of the energy absorbed by target gas molecules will result in the rise of gas temperature. Temperature fluctuations will produce a pressure wave which can be detected by a suitable sensor. By measuring pressure at different wavelengths, a photoacoustic spectrum of the target molecule can be obtained to determine the concentration.

The effects of background changes between measuring the background spectrum without the reactive gas and measuring the unaltered stream spectrum containing reactive gas can be minimized by taking into account that background gas compositions can change over time causing the 2f spectra lineshape to change due to the stream component concentration changes and associated broadening effects. In some implementations, if the background composition changes during the measurement interval, the resulting line shape variation could lead to measurement uncertainty resulting from using a direct subtraction between spectra with and without the reactive gas present. To minimize such measurement uncertainties, the present techniques can utilize background subtraction method comprising: (a) selection of a reference 2f peak of the interfering background gas, which does not have interference from the reactive gas, in the same laser scan, (b)

measurement of the reference peak height for both spectra with a reactive gas and spectra without the reactive gas present, (c) scaling of the recorded background 2f spectra based on the measured reference peak heights, and (d) determining reactive gas concentration using the differential signal based on the scaled spectra.

Figure 8:
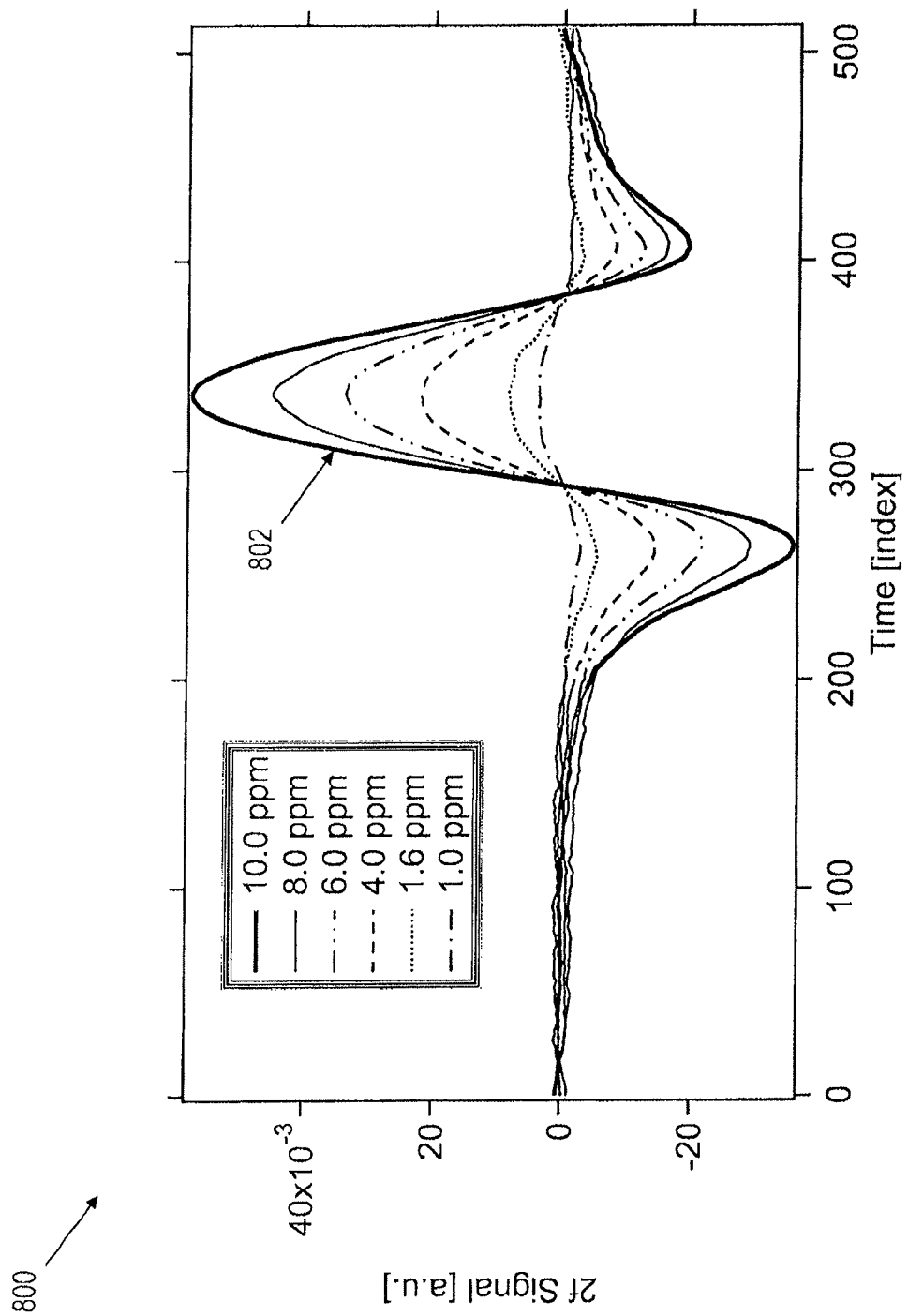
FIG. 8 is a chart showing differential absorption spectra for $H_2S$ at different concentrations.
Figure 9:
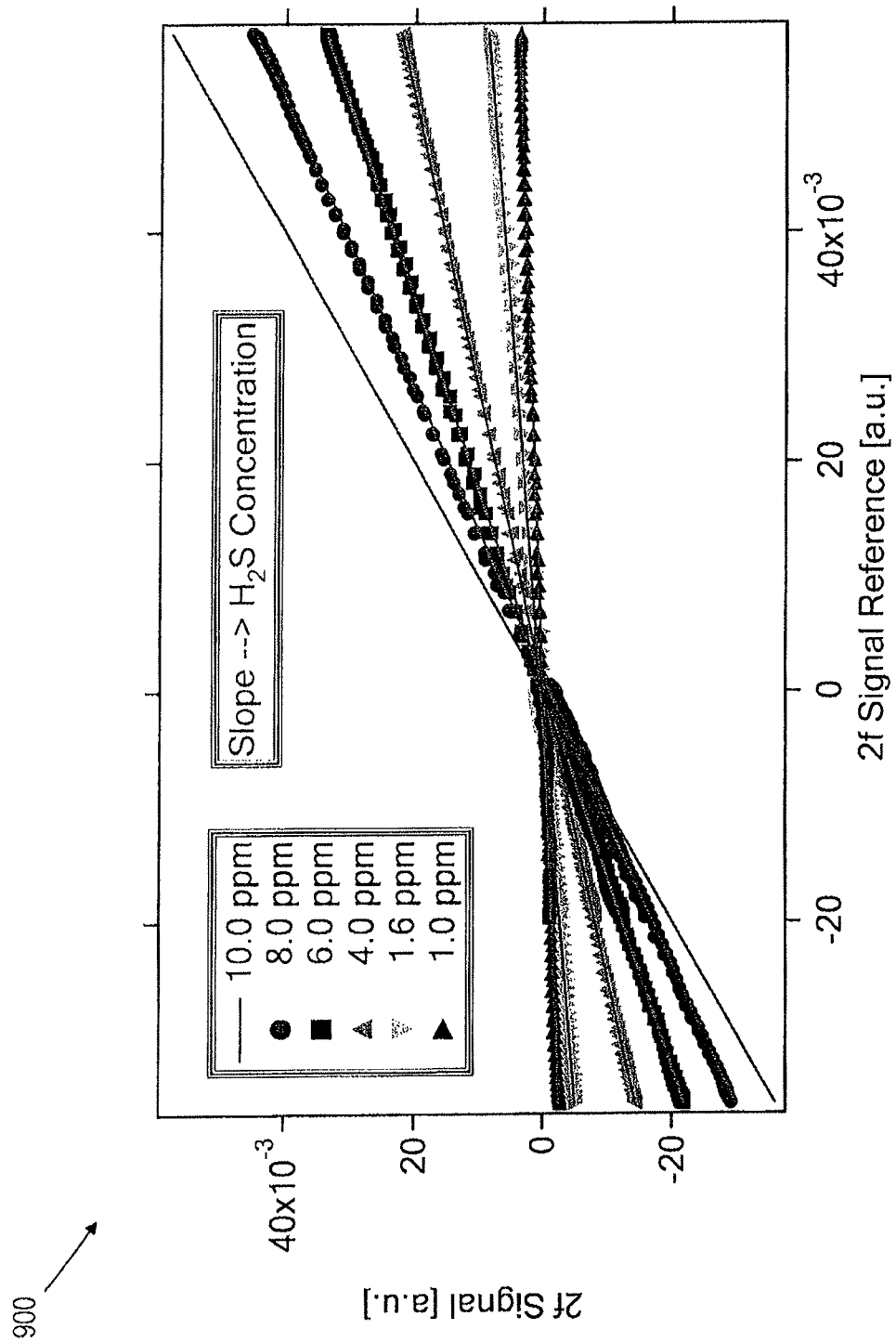
FIG. 9 is a chart showing calibration curves for $H_2S$.

A "curve fitting" method can be utilized to improve detection sensitivity and measurement repeatability. Even though the reactive gas concentration can be determined by only relying upon the calibrated 2f peak height, the measurement sensitivity and accuracy can in some cases be limited by noise on the differential 2f signal. The "curve fitting" method disclosed herein can include recording a reference differential spectra for a known concentration of the reactive gas, at a concentration where noise on the 2f signal is negligible. An $H_2S$ specific example is provided for illustration, but it will be understood that the general technique is applicable to all reactive gases analyzed using the current subject matter. FIG. 8 shows the $H_2S$ differential spectra at different $H_2S$ levels, the curve 802 representing 10 ppmv $H_2S$ in background gas, which can be used as the reference differential spectrum used for calibration. A curve fitting method can further include using this known concentration (for example 10 ppmv in FIG. 8) as a reference and plotting measured differential spectra vs. the reference spectra, since the amplitude of 2f spectra is proportional to the gas concentration, relationship between measured differential spectra and the reference spectra can be fitted well by a linear relationship as shown in FIG. 9. The reactive gas concentration can be determined from the ratio of the slope with respect to the reference concentration. This "curve fitting" method can use all or substantially all of the information available in the total 2f-line shape spectrum and greatly improves detection sensitivity and measurement repeatability. In some variations, the measured 2f lineshape can be best fitted directly with theoretical 2f models for Gaussian, Lorentzian or Voigt lineshapes. The theoretical 2f models are preferred but not limited to the models described in one or more of: L. C. Philippe and R. K. Hanson, "Laser Diode Wavelength-Modulation Spectroscopy for Simultaneous Measurement of Temperature, Pressure and Velocity in Shock-Heated Oxygen Flows," Applied Optics 32, 6090-6103 (1993); P. Kluczynski, A. M. Lindberg, and O. Axner, "Background signals in wavelength-modulation spectrometry with frequency-doubled diode-laser light I. Theory," Applied Optics, 783-793, Vol. 40, No. 6, 2001; and H. Li, G. B. Rieker, X. Liu, J. B. Jeffries, and R. K. Hanson, "Extension of wavelength modulation spectroscopy to large modulation depth for diode laser absorption measurements in high pressure gases," Applied Optics, 45, 1052, 2006, the contents of all of which are hereby incorporated by reference.

As the amount of light absorbed is proportional to the total path length the light travels through the sample gas, different absorption cells (such as for example a Herriott cell as discussed above) can be employed to obtain the necessary path length required by the desired sensitivity. The Herriott cell comprises two spherical mirrors spaced at a distance that enables a certain number of reflections of the laser beam before it meets the re-entrant condition and goes out of the cell cavity through the beam injection hole. With a Herriott cell, long optical paths can be achieved physically compact by reflecting the beam repeatedly without interference between adjacent beams. Depending on the desired sensitivity, the number of reflections of the Herriott cell can be adjusted by changing the spacing of the two mirrors, by changing the laser beam injection angle or by using mirrors with different focal lengths. Long effective pathlength can also be achieved by using off-axis resonating cavity which composes of two highly reflective mirrors. For calibration purposes, a controlled natural gas and other background gas samples containing a known concentration of the reactive gas can be passed through the absorption cell prior to measurements.

Frequency stabilization of a tunable laser light source can be critical for quantitative trace gas absorption spectroscopy. Depending on the operational wavelength, a tunable laser source such as a diode lasers can typically exhibit a wavelength drift on the order of a few picometers (on the order of gigahertz) per day to fractions of picometers per day. A typical trace gas absorption band linewidth can in some instances be on the order of a fraction of a nanometer to microns. Thus, drift of the laser light source can, over time, introduce critical errors in identification and quantification of trace gas analytes, particularly in gas having one or more background compounds whose absorption spectra might interfere with absorption features of a target analyte.

To address the above-noted and potentially other issues with currently available solutions, one or more further implementations of the current subject matter provide methods, systems, articles of manufacture, and the like that can, among other possible advantages, provide an automated, algorithmic approach that frequency stabilizes a tunable laser light source of a laser absorption spectrometer to improve the robustness of quantitative trace gas concentration measurements by compensating and/or correcting for short term ambient changes in analytical conditions as well as long term drift and aging effects that may adversely affect performance of the laser absorption spectrometer.

Real time laser frequency stabilization can be achieved in some implementations by comparing actual absorption spectra collected at the time of calibration of an instrument with absorption spectra collected in the field for gas samples without need for a molecular reference cell and a separate laser frequency stabilization circuit. Aside from increased cost and complexity, a separate laser frequency stabilization circuit can also interfere with the actual measurement. The current subject matter can reduce cost and complexity while also improving operating robustness and measurement fidelity and reproducibility compared to previously available spectroscopy approaches based on frequency stabilization onto a molecular line which is not part of the actual measurement. Using an approach as described herein, information about the performance of a laser spectrometer relative to a previous known or calibrated state can be obtained across the breadth of a scanned wavelength range of a tunable or scannable laser light source. Such an approach can provide substantial improvement relative to techniques that focus only on peak location rather than an entire absorption curve shape over a broader range of wavelengths.

Figure 10:
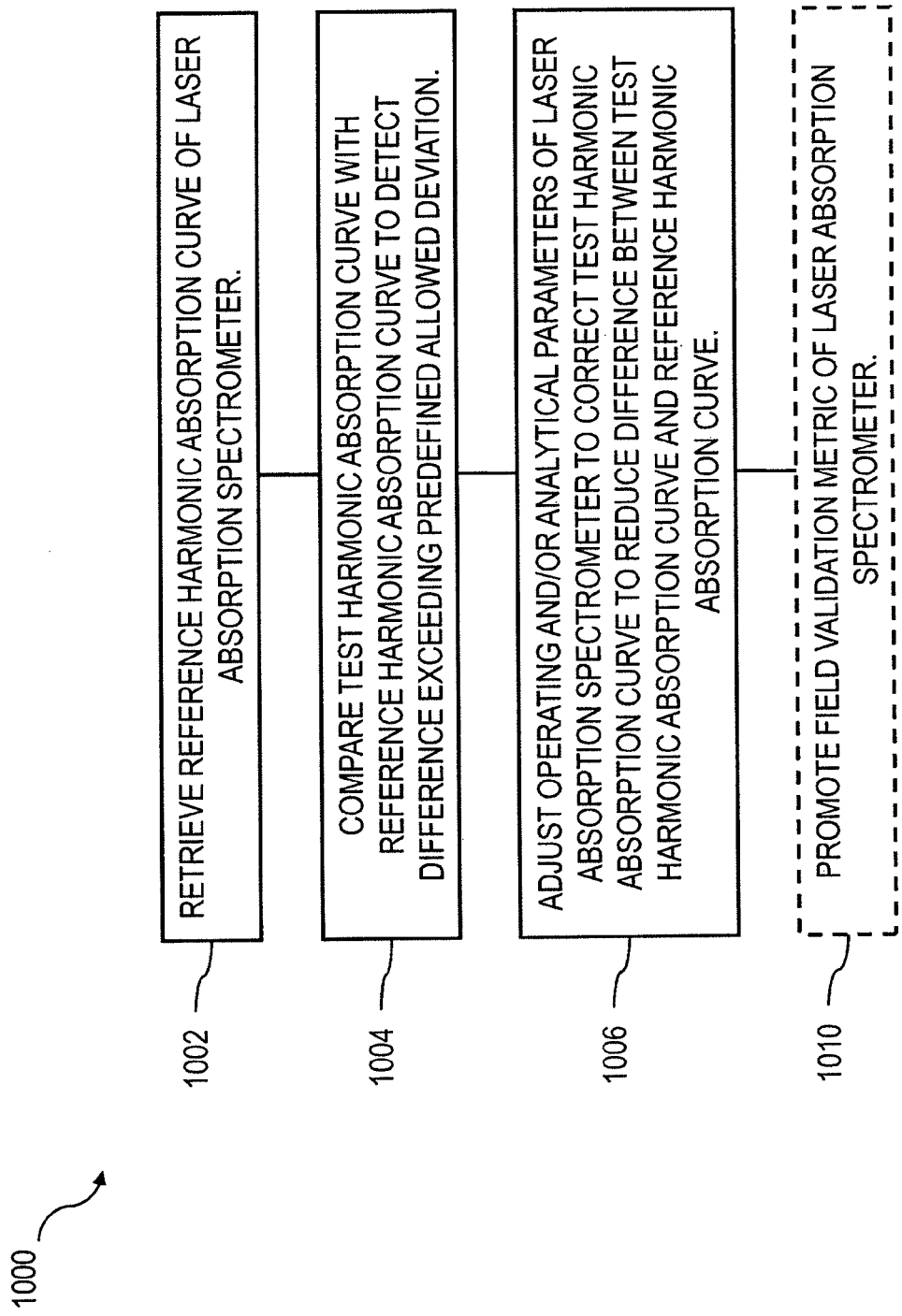
FIG. 10 illustrates a process flow diagram illustrating aspects of a method consistent with implementations of the current subject matter.

FIG. 10 shows a process flow chart 1000 illustrating features consistent with an implementation of the current subject matter. At 1002, one or more reference harmonic absorption curves that can be obtained through analysis of one or more reference gas mixtures by a laser absorption spectrometer is/are retrieved, for example from local or networked data storage. The one or more reference harmonic absorption curves that can have been previously obtained through analysis of one or more reference gas mixtures by a laser absorption spectrometer, for example at factory calibration or at another time when the laser absorption spectrometer is in a well-calibrated state, and stored for later retrieval. At 1004, a test harmonic absorption curve is compared with the at least one of the one or more reference harmonic absorption curves to detect a difference between the respective curve shapes that exceeds a predefined allowed deviation. At 1006, the operating and/or analytical parameters of the laser absorption spectrometer are adjusted to correct the test harmonic absorption curve to reduce the detected difference between the test harmonic absorption curve shape and the reference harmonic absorption curve shape. In other words, after adjusting of the one or more operating and/or analytical parameters of the laser absorption spectrometer, a subsequent test harmonic absorption curve more closely resembles the reference harmonic absorption curve. Optionally, at 1010, a field validation metric of the laser absorption spectrometer can be promoted. The field validation metric can include at least one of the difference between the test curve shape and the reference curve shape, an identification of the one or more operating and analytical parameters that were adjusted, and a value by which the one or more operating and analytical parameters were adjusted.

The adjusting of the one or more operating and/or analytical parameters of the laser absorption spectrometer to reduce the detected difference between the test harmonic absorption curve shape and the reference harmonic absorption curve shape can be performed by a variety of approaches. In one implementation, an iterative approach can be used. In one non-limiting implementation, one of several potential operating and/or analytical parameters of the laser absorption spectrometer can be adjusted and a new test harmonic absorption curve generated by the laser absorption spectrometer. Adjustments to the selected parameter can continue with successive generation of new test harmonic absorption curves until a setting of maximum improvement in the difference between a test harmonic absorption curve and the reference harmonic absorption curve is obtained. Then another parameter can be iteratively adjusted in a similar manner until each parameter has been so adjusted. Any algorithm usable for iteratively converging to a multi-variate solution can be used.

The test curve can be collected using a reference gas with known concentration of a target analyte, or with a sample gas having a known or unknown concentration of the analyte or even not containing the analyte (i.e., only the background gas or mixture). If the test curve is collected with a unknown concentration of the target analyte, a reference curve can be constructed using one or more stored reference curves according to a previously measured target analyte concentration (i.e. the target analyte concentration obtained for a measurement immediately or otherwise proceeding the current measurement) and then compare the test curve with the constructed reference curve. Alternatively, only part of the test curve that is not affected by the concentration of the analyte can be compared. For example, the part of the curve that arises only due to absorption of the background gases.

The exact shape of the test curve, and the concentration calculation of the one or more target analytes for which the laser absorption spectrometer is configured to analyze can depend critically upon the laser frequency behavior. The laser frequency behavior can be affected by one or more operating and environmental parameters that can include, but are not limited to the center frequency, the ramp current, the modulation current, and other parameters of the laser light source as well as one or more parameters of the sample cell, detector, demodulator, and the like. The center frequency of the laser light source can be affected by at least the operating temperature and the operating current of the laser light source. The particular frequency changes caused by changes in drive and/or modulation current, temperature, and the like can be quite specific to each individual laser light source.

A curve correlation algorithm according to implementations of the current subject matter can generate an error signal whenever the laser frequency changes, (i.e. if the same reference gas that was used to record the original reference trace is periodically analyzed). The reference harmonic absorption curve can be stored once, when the analyzer receives its original calibration in the factory. Alternatively or in addition, the reference harmonic absorption curve can be updated periodically using a differential spectroscopy approach, for example as described above to adjust for stream changes, while maintaining a basic reference from the original calibration.

Upon receiving an error signal, an optimization algorithm can engage to adjust or otherwise reset one or more operating and analytical parameters of the laser absorption spectrometer, which can include but are not limited to laser temperature, operating current, modulation current, ramp current, and other signal detection and conversion parameters, to automatically reconstruct the exact harmonic absorption curve shape as was originally stored during factory calibration.

Figure 11:
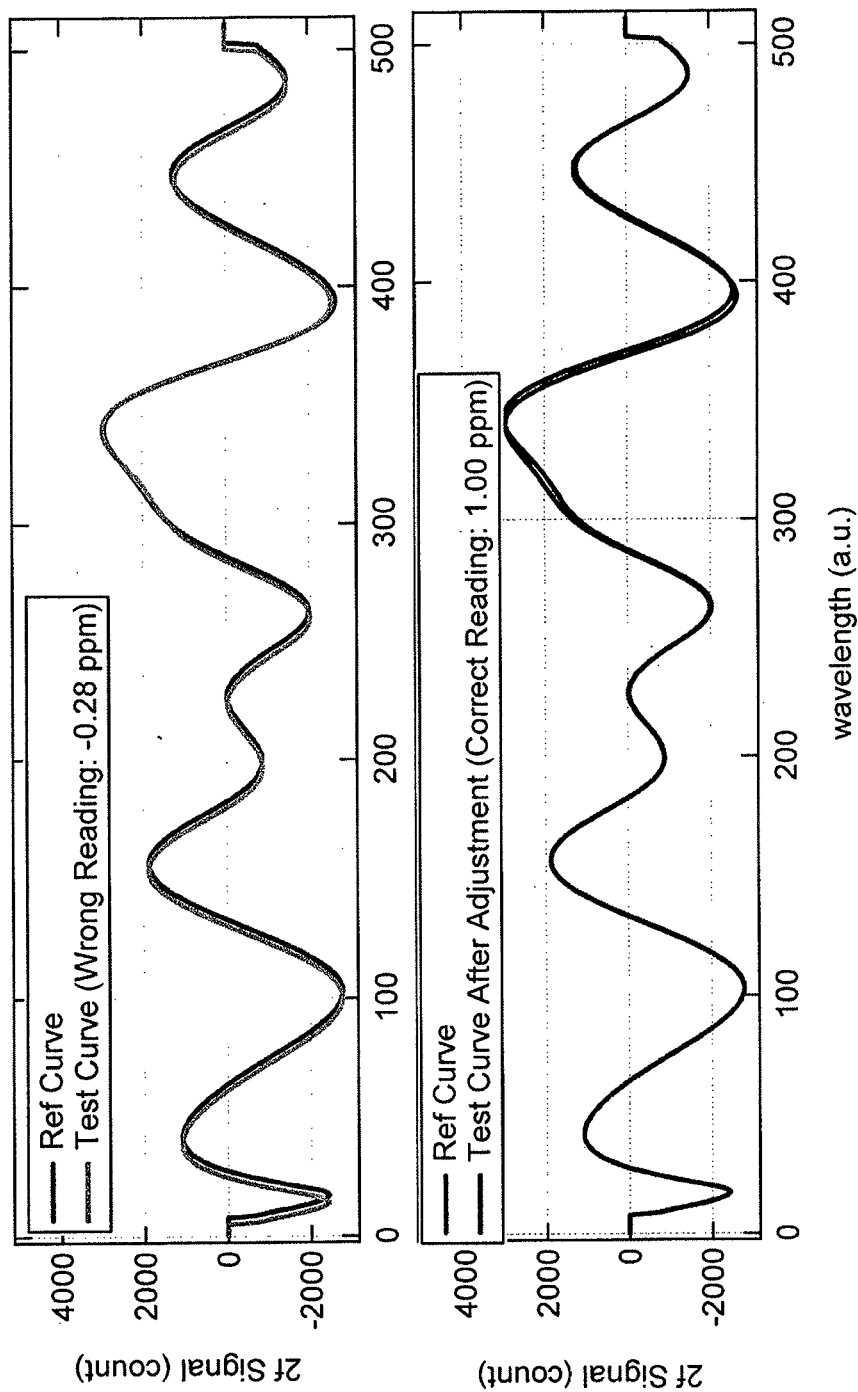
FIG. 11 illustrates two spectral absorption charts showing an example of adjusting a middle operating current of a laser light source to shift a test curve to align with a stored reference curve.
Figure 12:
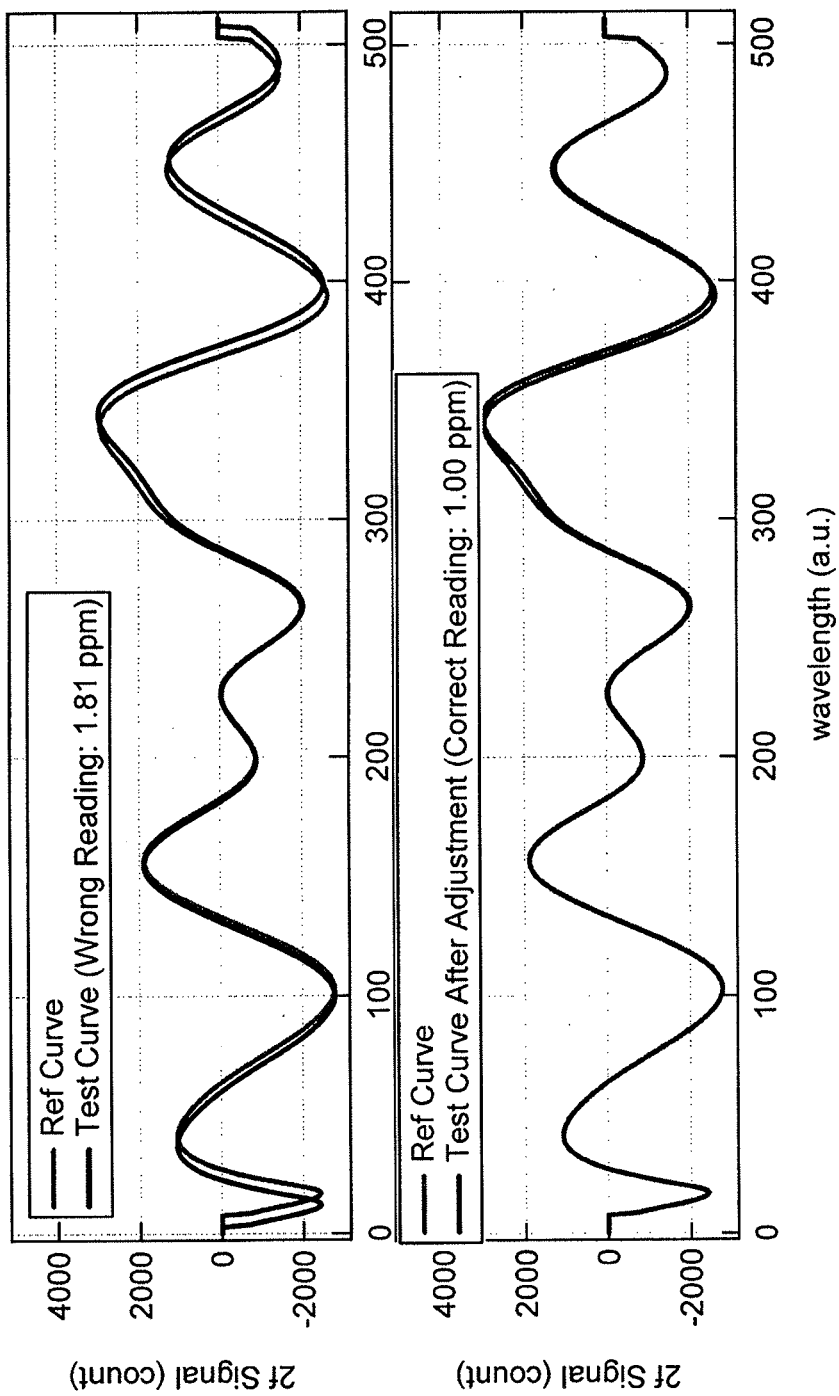
FIG. 12 is two spectral absorption charts showing an example of adjusting one or more operating parameters of a laser light source and/or signal converting parameters to correct a test curve shape to reduce the difference between the test curve shape and a reference curve shape.

FIG. 11 and FIG. 12 show two examples of dynamic corrections to a calibration state of a spectrometer using sample data. The reference curve shown in the top and bottom panels of FIG. 11 is obtained with a tunable diode laser spectrometer for a reference gas mixture containing approximately 25% ethane and 75% ethylene. The test curve shown on the top panel of FIG. 11 is obtained using the same spectrometer after some time had passed for a test gas mixture containing 1 ppm acetylene in a background of approximately 25% ethane and 75% ethylene. Acetylene has a spectral absorption feature in the range of about 300 to 400 on the wavelength axis of the charts in FIG. 11. In an example in which drift and/or other factors affect the spectrometer performance over time, the test curve can be shifted (for example to the left as shown in FIG. 11) compared with the reference curve. Absent a correction to the test curve, the measured concentration of acetylene from the spectrometer would be −0.29 ppm instead of the correct value of 1 ppm.

According to an approach consistent with implementations of the current subject matter, the amount of the test curve drift can be identified by comparing the test and reference curves in a portion of the spectrum outside of the area where the acetylene absorption feature occurs (i.e. the region between about 20-260 on the wavelength axis). The laser middle operating current can be adjusted to shift the test curve back to align up with the reference curve as shown in the bottom panel of FIG. 11. After the adjustment, the measured concentration of acetylene from the spectrometer is 1 ppm.

The reference curve in the top and bottom panels of FIG. 12 is also obtained with a tunable diode laser spectrometer for a reference gas mixture containing approximately 25% ethane and 75% ethylene. The test curve on the top panel of FIG. 12 was obtained for a test gas mixture containing 1 ppm acetylene in a background of approximately 25% ethane and 75% ethylene. As shown in the top panel of FIG. 12, the test curve shape is distorted relative to the shape of the reference curve due to drift or other factors affecting performance of the laser absorption spectrometer over time. If the test curve is not corrected, the measured concentration of acetylene in the test gas mixture determined by the spectrometer can be, for example, 1.81 ppm instead of the true concentration of 1 ppm.

According to an approach consistent with implementations of the current subject matter, the amount of test curve distortion can be identified and/or corrected for by comparing one or more sections of the test curve and reference curve in one or more portions of the spectrum outside of the area where the acetylene absorption feature occurs (i.e. the regions between about 20-260 and 400-500 on the wavelength axis). The laser operating parameters and signal converting parameters can be adjusted to correct the test curve shape to more closely resemble the reference curve shape. After the adjustment, the measured concentration of acetylene from the spectrometer turns to 1 ppm.

The approaches illustrated in FIG. 11 and FIG. 12 use a reference harmonic spectrum collected for a sample having a background composition consistent with that expected to be present under analytical conditions during which the target analyte (acetylene) is to be quantified. In an alternative or additional implementation, the reference harmonic spectra can be selected to contain one or more background absorption peaks that do not change with background compositions. In an alternative or additional implementation, the reference harmonic spectrum can be constructed from reference absorption spectra of individual background species.

As described and illustrated, implementations of the current subject matter can consider substantially more information regarding the exact shape of a reference harmonic absorption curve than is typically used in peak locking. Previously available laser control loops are generally limited to only stabilizing or tracking the laser frequency and/or peak position (i.e. location of the peak of a spectral feature in the digitized scan range of the measurement).

The approach described herein can be applicable to any laser absorption spectrometer that includes a tunable laser source, including but not limited to direct absorption spectrometers, harmonic absorption spectrometers, differential absorption spectrometers, etc. For a direct absorption spectrometer, the measurement of target analyte concentrations can be performed without using a harmonic conversion or demodulation of the signal obtained from the detector. However, periodic or continuous recalibration of the laser light source, detector, etc. can be performed using a calibration circuit, etc. that makes use of a harmonic signal obtained from the detector signal.

In another implementation, the calibration state of a harmonic absorption spectrometer can be validated using different operating parameters, including but limited to the modulation frequency, ramp frequency, etc., than are used in identifying and/or quantifying a target analyte. Use of larger modulation frequencies can increase the signal to noise ratio of an absorption feature of a target analyte by relatively reducing the impact of absorption by the background composition of a gas mixture. However, as the current subject matter can make use of information obtained from all absorption features that occur across a laser scan range in verifying agreement between a test harmonic absorption curve and a reference harmonic absorption curve, it can be advantageous to collect both the test and reference harmonic absorption curves under conditions that lead to a more complicated spectrum so that additional features are available to be matched between the test and reference harmonic absorption curves.

Aspects of the subject matter described herein can be embodied in systems, apparatus, methods, and/or articles depending on the desired configuration. Some implementations of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments can be within the scope of the following claims.

What is claimed:

1. A method comprising:

collecting a first sample absorption data set for a first sample of a gas mixture that comprises a reactive gas at a reactive gas concentration and a first background composition that contributes spectral interference that hampers direct spectroscopic measurement of the reactive gas concentration in the gas mixture, the collecting comprising passing light from a tunable or scannable laser light source operating in a scan range through at least part of the first sample such that the light reaches a detector after passing through the at least part of the first sample, the first sample absorption data set comprising a test harmonic absorption curve having a test curve shape;

retrieving, by a computer processor, a reference harmonic absorption curve of a laser absorption spectrometer comprising the tunable or scannable laser light source and the detector, the reference harmonic absorption curve having a reference curve shape and comprising a first, a second, or a higher order harmonic signal of a reference signal generated by the detector in response to light passing from the laser light source through a reference gas or gas mixture, the reference gas or gas mixture comprising one or more of the reactive gas and the background composition; the reference harmonic absorption curve having been determined for the laser absorption spectrometer in a known or calibrated state;

comparing the test harmonic absorption curve with the reference harmonic absorption curve to detect a difference between the test curve shape and the reference curve shape that exceeds a predefined allowed deviation and therefore indicates a change in an output of the laser light source relative to the known or calibrated state;

adjusting one or more operating and/or analytical parameters of the laser absorption spectrometer to reduce the difference between the test curve shape and the reference curve shape;

collecting a second sample absorption data set for the first sample or a second sample using the adjusted one or more operating and/or analytical parameters;

generating a differential absorption spectrum by adjusting the second sample absorption data set using a background absorption data set comprising data characteristic of absorption characteristics of the first background composition; and converting the first differential absorption spectrum to a first measured concentration of the reactive gas in the gas mixture using calibration data.

2. A method as in claim 1, wherein the background absorption data set comprises empirically obtained historical absorption data for a first characteristic background composition representative of the first background composition.

3. A method as in claim 1, wherein the first sample absorption data set and the background absorption data set are harmonic absorption spectra, and wherein the converting of the first differential absorption spectrum to the first measured concentration of the reactive gas in the gas mixture further comprises:

determining a best fit slope of a line comprising first data points of the first differential absorption spectrum plotted against a reference differential spectra obtained for a known concentration of the reactive gas; and calculating the first measured concentration based on a ratio of the best fit slope to a reference slope that is equal to one.

4. A method as in claim 1, further comprising collecting the first background absorption data for a first background sample prepared from the gas mixture, the collecting comprising using the tunable or scannable laser in the scan range, the preparing of the first background sample comprising treating a volume of the gas mixture to reduce a concentration of the reactive gas without substantially altering the first background composition in the first background sample.

5. A method as in claim 1, wherein generating the differential absorption spectrum further comprises: detecting a second order or higher harmonic frequency response of light passing through the first sample from a scannable laser to the detector, a wavelength of the tunable or scannable laser being modulated at a modulation frequency; and converting the second order or higher harmonic frequency response to the second sample absorption data set.

6. A method as in claim 1, further comprising: promoting a field validation metric of the laser absorption spectrometer, the field validation metric comprising at least one of the difference between shapes of the test harmonic absorption curve and the reference harmonic absorption curve, an identification of the one or more adjusted operating and/or analytical parameters, and a value by which the one or more operating and/or analytical parameters were adjusted.

7. A method as in claim 1, wherein the adjusting comprises an iterative approach comprising:

making an adjustment to a selected one of a plurality of operating and/or analytical parameters of the laser absorption spectrometer, generating a new test harmonic absorption curve by the laser absorption spectrometer; and successively making one or more additional adjustments to the selected one operating and/or analytical parameter and generating another new test harmonic absorption curve until a setting of the selected one operating and/or analytical parameter is found that causes a maximum improvement in the difference between a resultant test harmonic absorption curve and the reference harmonic absorption curve.

8. A method as in claim 7, wherein the iterative approach further comprises:

making a second adjustment to a second selected one of a plurality of operating and/or analytical parameters of the laser absorption spectrometer, generating a second new test harmonic absorption curve by the laser absorption spectrometer; and successively making one or more second additional adjustments to the second selected one operating and/or analytical parameter and generating another second new test harmonic absorption curve until a setting of the second selected one operating and/or analytical parameter is found that causes a second maximum improvement in the difference between a second resultant test harmonic absorption curve and the reference harmonic absorption curve.

9. A method as in claim 1, further comprising: constructing the reference harmonic absorption curve, the constructing comprising using one or more stored reference curves combined according to a previously measured target analyte concentration.

10. A method as in claim 9, wherein the previously measured target analyte concentration results from a measurement preceding a current measurement.

11. A method as in claim 1, further comprising updating the reference harmonic absorption curve using a differential spectroscopy approach to adjust for changes in the first background composition.

12. An article of manufacture comprising a tangibly embodied machine-readable medium encoding instructions that, when executed by a programmable system comprising one or more processors, cause the programmable system to perform operations comprising:

collecting a first sample absorption data set for a first sample of a gas mixture that comprises a reactive gas at a reactive gas concentration and a first background composition that contributes spectral interference that hampers direct spectroscopic measurement of the reactive gas concentration in the gas mixture, the collecting comprising passing light from a tunable or scannable laser light source operating in a scan range through at least part of the first sample such that the light reaches a detector after passing through the at least part of the first sample, the first sample absorption data set comprising a test harmonic absorption curve having a test curve shape;

retrieving, by a computer processor, a reference harmonic absorption curve of a laser absorption spectrometer comprising the tunable or scannable laser light source and the detector, the reference harmonic absorption curve having a reference curve shape and comprising a first, a second, or a higher order harmonic signal of a reference signal generated by the detector in response to light passing from the laser light source through a reference gas or gas mixture, the reference gas or gas mixture comprising one or more of the reactive gas and the background composition; the reference harmonic absorption curve having been determined for the laser absorption spectrometer in a known or calibrated state;

comparing the test harmonic absorption curve with the reference harmonic absorption curve to detect a difference between the test curve shape and the reference curve shape that exceeds a predefined allowed deviation and therefore indicates a change in an output of the laser light source relative to the known or calibrated state;

adjusting one or more operating and/or analytical parameters of the laser absorption spectrometer to reduce the difference between the test curve shape and the reference curve shape;

collecting a second sample absorption data set for the first sample or a second sample using the adjusted one or more operating and/or analytical parameters;

generating a differential absorption spectrum by adjusting the second sample absorption data set using a background absorption data set comprising data characteristic of absorption characteristics of the first background composition; and converting the first differential absorption spectrum to a first measured concentration of the reactive gas in the gas mixture using calibration data.

13. A system comprising:

a programmable system comprising one or more processors;

a machine-readable medium encoding instructions that, when executed by the programmable system, cause the programmable system to perform operations comprising:

collecting a first sample absorption data set for a first sample of a gas mixture that comprises a reactive gas at a reactive gas concentration and a first background composition that contributes spectral interference that hampers direct spectroscopic measurement of the reactive gas concentration in the gas mixture, the collecting comprising passing light from a tunable or scannable laser light source operating in a scan range through at least part of the first sample such that the light reaches a detector after passing through the at least part of the first sample, the first sample absorption data set comprising a test harmonic absorption curve having a test curve shape;

retrieving, by a computer processor, a reference harmonic absorption curve of a laser absorption spectrometer comprising the tunable or scannable laser light source and the detector, the reference harmonic absorption curve having a reference curve shape and comprising a first, a second, or a higher order harmonic signal of a reference signal generated by the detector in response to light passing from the laser light source through a reference gas or gas mixture, the reference gas or gas mixture comprising one or more of the reactive gas and the background composition; the reference harmonic absorption curve having been determined for the laser absorption spectrometer in a known or calibrated state;

comparing the test harmonic absorption curve with the reference harmonic absorption curve to detect a difference between the test curve shape and the reference curve shape that exceeds a predefined allowed deviation and therefore indicates a change in an output of the laser light source relative to the known or calibrated state;

adjusting one or more operating and/or analytical parameters of the laser absorption spectrometer to reduce the difference between the test curve shape and the reference curve shape;

collecting a second sample absorption data set for the first sample or a second sample using the adjusted one or more operating and/or analytical parameters;

generating a differential absorption spectrum by adjusting the second sample absorption data set using a background absorption data set comprising data characteristic of absorption characteristics of the first background composition; and converting the first differential absorption spectrum to a first measured concentration of the reactive gas in the gas mixture using calibration data.

14. A system as in claim 13, further comprising: the tunable or scannable laser source operating in a scan range that comprises a target wavelength; and the detector is positioned to receive and quantify an intensity of light from the tunable or scannable laser source after the light passes through a sample volume of the reactive gas.

15. A system as in claim 13, further comprising:

one or more valves; and a scrubber material that converts molecules of the reactive gas to a non-gaseous state; and wherein the operations further comprise:

controlling the one or more valves to direct a first background sample of the reactive gas through the scrubber material to reduce a concentration of the reactive gas in the first background sample without substantially altering the first background composition in the first background sample; and collecting the first sample absorption data set by quantifying the intensity of light from the tunable or scannable laser source reaching the detector through the first sample; and collecting the first background absorption data set by quantifying the intensity of light from the tunable or scannable laser source reaching the detector through the first background sample.

16. A system as in claim 15, wherein the scrubber material comprises one or more of metal oxides, cupric dicarbonate, solid and liquid-phase inorganic and organic acids and bases, metal oxide and copper oxide nano particles suspended on larger grain size carrier particles, solid state scrubbers, liquid scrubbers, amine solutions, aqueous ammonia solutions, and aqueous solutions of strong acids or bases.

17. A system as in claim 15, further comprising a single sample cell that alternately contains the first sample and the first background sample during the collecting of the first or the second sample absorption data set and the collecting of the first background absorption data set, respectively.

18. A system as in claim 15, further comprising a sample cell that contains the first sample during the collecting of the first or the second sample absorption data set and a background sample cell that contains the background sample during the collecting of the first background absorption data set, the sample cell and the background sample cell having substantially identical optical path lengths.

* * * * *